US008440191B2

(12) United States Patent
Plaut et al.

(10) Patent No.: US 8,440,191 B2
(45) Date of Patent: May 14, 2013

(54) CLEARANCE OF ABNORMAL IGA1 IN IGA1 DEPOSITION DISEASES

(75) Inventors: Andrew G. Plaut, Lexington, MA (US); Jiazhou Qiu, Westborough, MA (US)

(73) Assignee: Tufts Medical Center, Boston, MA (US)

( * ) Notice: Subject to any disclaimer, the term of this patent is extended or adjusted under 35 U.S.C. 154(b) by 879 days.

(21) Appl. No.: 12/094,145

(22) PCT Filed: Nov. 17, 2006

(86) PCT No.: PCT/US2006/044844
§ 371 (c)(1), (2), (4) Date: May 6, 2009

(87) PCT Pub. No.: WO2007/061936
PCT Pub. Date: May 31, 2007

(65) Prior Publication Data
US 2009/0317381 A1 Dec. 24, 2009

Related U.S. Application Data

(60) Provisional application No. 60/737,984, filed on Nov. 18, 2005.

(51) Int. Cl.
*A61K 39/395* (2006.01)
(52) U.S. Cl.
USPC ............... 424/133.1; 424/139.1; 424/141.1; 424/145.1; 424/804; 424/810; 514/15.4
(58) Field of Classification Search .................. None
See application file for complete search history.

(56) References Cited

U.S. PATENT DOCUMENTS

| 5,079,344 | A | * | 1/1992 | Chang et al. ............. 530/388.25 |
| 5,413,918 | A | | 5/1995 | Faulmann |
| 5,534,544 | A | | 7/1996 | Plaut et al. |
| 7,407,653 | B2 | | 8/2008 | Plaut et al. |
| 2003/0035800 | A1 | | 2/2003 | Leung et al. |

FOREIGN PATENT DOCUMENTS

| EP | 2 042 513 A1 | 4/2009 |
| WO | 90/11367 A1 | 10/1990 |
| WO | 00/63383 A1 | 10/2000 |
| WO | 2004/096157 A2 | 11/2004 |

OTHER PUBLICATIONS

Turkova J., 1999, Journal of Chromatography B, 722:11-31.*
Kokubo et al., Nephrol Dial Transplant. Jan. 1999;14(1):81-5.*
Delente, Trends in Biotechnology 3, 9, 1985.*
Olden et al. Biochem et Biophys Acta vol. 650, 1982. 209-232.*
Wright et al., Springer Semin Immunopathology, 1993, vol. 15:259-273.*
Rudikoff et al., Proc. Natl. Acad. Sci. USA, 1982, pp. 1979-1983.*
Allen et al., "Galactosylation of N- and O-linked carbohydrate moieties of IgA1 and IgG in IgA nephropathy", Clin. Exp. Immunol., 100:470-474 (1995).
Appel et al., "The IgA nephropathy treatment dilemma", Kidney Int., 69(11):1939-1944 (2006).
Ballardie, "IgA nephropathy treatment 25 years on: can we halt progression? The evidence base", Nephrol. Dial. Transplant., 19(5):1041-1046 (2004).
Barratt et al., "IgA Nephropathy", J. Am. Soc. Nephrol., 16:2088-2097 (2005).
Barratt et al., "Immunopathogenesis of IgAN", Semin. Immunopathol., 29:427-443 (2007).
Coppo et al., "Aberrant glycosylation in IgA nephropathy (IgAN)", Kidney Int., 65(5):1544-1547 (2004).
Database Uniprot (online) Sep. 5, 2006 XP002595606, Database accession No. QOPVD5, abstract.
Definition: "focal glomerulonephritis" In: Stedman's medical dictionary Ed 26 1995 pp. 727.
Galye et al., "Identification of regions in interleukin-1 alpha important for activity", J. Biol. Chem., 268(29):22105-22111 (1993).
Gesualdo et al., "Enzymolysis of Glomerular Immune Deposits in Vivo with Dextranase/Protease Ameliorates Proteinuria, Hematuria, and Mesangial Proliferation in Murine Experimental IgA Nephropathy", J. Clin. Invest., 86:715-722 (1990).
Govindan et al., "Use of Galactosylated-Streptavidin as a Clearing Agent with 111In-Labeled, Biotinylated Antibodies to Enhance Tumor/Non-Tumor Localization Ratios", Cancer Biotherapy & Radiopharmaceuticals, 17(3):307-316 (2002).
Grundy et al., "Localization of the cleavage site specificity determinant of *Haemophilus influenza* immunoglobulin A1 protease genes", Infect. Immun., 58(2):320-331 (1990).
Halter et al., "IgA protease of *Neisseria gonorrhoeae*: isolation and characterization of the gene and its extracellular product", EMBO J., 3(7):1595-1601 (1984).
Hsu et al., "The molecular pathogenesis and experimental therapy of IgA nephropathy: recent advances and future directions", Curr. Mol. Med., 1(2):183-196 (2001).
Julian et al., "IgA nephropathy: an update", Curr. Opin. Nephrol. Hypertens., 13:171-179 (2004).
Kilian et al., "Pathogenic species of the genus *Haemophilus* and *Streptococcus pneumoniae* produce immunoglobulin Al protease", Infect. Immun., 26(1):143-149 (1979).
Kilian et al., "IgA1 proteases from *Haemophilus influenza, Streptococcus pneumoniae, Neisseria meningitis,* and *Streptococcus sanguis*: comparative immunochemical studies" J. Immunol. 124(6):2596-2600 (1980).

(Continued)

*Primary Examiner* — Michael Szperka
(74) *Attorney, Agent, or Firm* — Choate, Hall & Stewart, LLP

(57) ABSTRACT

The present invention relates to proteins which specifically bind to IgA1 and which have been modified to comprise either O- or N-linked glycans. The invention encompasses methods for decreasing IgA1, preferably abnormally glycosylated IgA1, in an individual by administering to the individual a glycan-modified IgA1 binding protein of the invention. The invention also encompasses a method for the treatment of a disease characterized by IgA1 deposition wherein a glycan-modified IgA1 binding protein is administered to an individual in need thereof.

33 Claims, 6 Drawing Sheets

OTHER PUBLICATIONS

Kobayashi et al., "IgA protease from Clostridium ramosum that cleaves IgA1 and IgA2, A2m(1): the site of cleavage and digestion of secretory IgA", Adv. Exp. Med. Biol., 216B:1289-1296 (1987).

Kojima et al., "Enhancement of clearance of plant lectins as radiopharmaceuticals by chemically glycosylated antilectin antibody", Eur. J. Nucl. Med., 15:373-375 (1989).

Kokubo et al., "Humoral immunity against the proline-rich peptide epitope of the IgA1 hinge region in IgA nephropathy", Nephrol. Dial. Transplant, 15:28-33 (2000).

Koshland et al., "Selective proteolysis of the J chain component in human polymeric immunoglobin", J. Immunol., 118 (3):775-781 (1977).

Lamm et al., "Microbial IgA Protease Removes IgA Immune Complexes from Mouse Glomeruli in Vivo: Potential Therapy for IgA Nephropathy", Am. J. Pathol., 172(1):31-36 (2008).

Launay et al., "Fcalpha receptor (CD89) mediates the development of immunoglobulin A (IgA) nephropathy (Berger's disease). Evidence for pathogenic soluble receptor-Iga complexes in patients and CD89 transgenic mice", J. Exp. Med., 191(11):1999-2009 (2000).

Medzihradszky et al., "Glycoforms obtained by expression in Pichia pastoris improve cancer targeting potential of a recombinant antibody-enzyme fusion protein", Glycobiology, 14(1):27-37 (2004).

Mestecky et al., "Defective Galactosylation and Clearance of IgA1 Molecules as a Possible Etiopathogenic Factor in IgA Nephropathy", Contributions of Nephrology, 104:172-182 (1993).

Michael et al., "Recurrent haematuria: role of renal biopsy and investigative morbidity", Br. Med. J., 1:686-688 (1976).

Moura et al., "Glycosylation and Size of IgA1 are Essential for Interaction with Mesangial Transferrin Receptor in IgA Nephropathy", J. Am. Nephrol., 15:622-634 (2004).

Nakazawa et al., "Proteolytic enzyme treatment reduces glomerular immune deposits and proteinuria in passive Heymann nephritis", J. Exp. Med., 164:1973-1987 (1986).

Nikolova et al., "The role of the carbohydrate chains in complement (C3) fixation by solid-phase-bound human IgA", Immunology, 82:321-327 (1994).

Piesecki et al., "Immobilization of beta-galactosidase for application in organic chemistry using a chelating peptide", Biotech. & Bioeng., 42(2):178-184 (1993).

Plaut et al., "Human lactoferrin proteolytic activity: analysis of the cleaved region in the IgA protease of *Haemophilus influenzae*", Vaccine, 19:S148-S152 (2001).

Rostoker et al. "High-dose immunoglobulin therapy for severe IgA nephropathy and Henoch-Schönlein purpura", Ann. Intern. Med., 120(6):476-484 (1994).

Smith et al., "New insights into the pathogenesis of IgA nephropathy", Springer Semin. Immunopathol., 24:477-493 (2003).

Strauss et al., "C-terminal glycine-histidine tagging of the outer membrane protein Iga beta of *Neisseria gonorrhoeae*", FEMS Microbiol. Lett., 127(3):249-254 (1995).

Whisstock et al., "Prediction of protein function from protein sequence and structure", Q. Rev. Biophys., 36 (3):307-340 (2003).

International Search Report for PCT/US04/06615, dated Aug. 16, 2005.

International Search Report for PCT/US2010/031733, mailed Nov. 17, 2010.

International Preliminary Report on Patentability for PCT/US2010/031733, mailed Nov. 3, 2011.

* cited by examiner

Figure 1: Dimeric IgA1, its hinge region sequence, and the O-glycan sites (Ọ)

Figure 3.

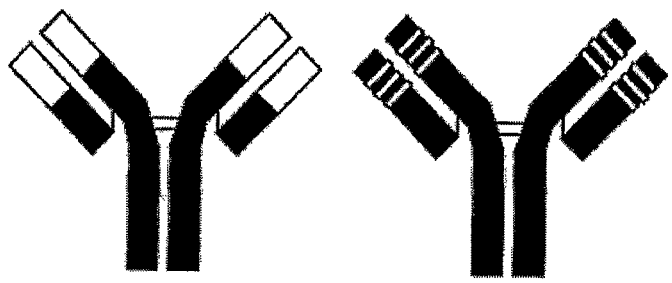

Figure 6. Schematic representation of humanised antibodies, chimeric (left) and fully reshaped (right). In the case of the chimeric antibody the rodent heavy ($V_H$) and light chain ($V_L$) variable regions (white) are attached to human constant regions (black). After full reshaping the four framework regions within each V region are humanised leaving only the six complementarity determining regions (CDR) three in the heavy chain and three in the light chain (white).

Figure 4.

SEQ ID NO: 1 – SIR22

```
          5         10        15        20        25        30
    1   M A R K D T N K Q Y S L R K L K T G T A S V A V A V L G
   31   A G F A N Q T T V K A E S S N N A E S S N I S Q E S K L I N
   61   T L T D E N E K L R E E L Q Q Y Y A L S D A K E E E P R Y K
   91   A L R G E N Q D L R E K E R K Y Q D K I K K L E E K E K N L
  121   E K K S E D V E R H Y L K K L D Q E H K E Q Q E R Q K N L E
  151   E L E R Q S Q R E I D K R Y Q E Q L Q K Q Q Q L E T E K Q I
  181   S E A S R K S L S R D L E A S R A A K K K V E A D L A A L N
  211   A E H Q K L K E E K Q I S D A S R Q G L S R D L E A S R E A
  241   K K K V E A D L A E A N S K L Q A L E K L N K E L E E G K K
  271   L S E K E K A E L Q A R L E A E A K A L K E Q L A K Q A E E
  301   L A K L K G N Q T P N A K V A P Q A N R S R S A M T Q Q K R
  331   T L P S T G E A A N P F F T A A A A T V M V S A G M L A L K
  361   R K E E N
```

SEQ ID NO: 2 – SIR22 IgA1 binding protein

```
Y Y A L S D A K E E E P R Y K A L R G E N Q D L R E K E R K Y Q
D K I K K L E E K E K N L E K K S
```

SEQ ID NO: 3 – SIR22 Nucleic acid sequence

```
    1   AAGCTTCAGG AGCTCAAAAA CCAGATACTA AACCTGGCAA TAAAGAGGTT CCAACAAGAC
   61   CATCACAAAC AAGAACAAAC ACTAATAAAG CTCCTATGGC GCAAACAAAG AGACAATTAC
  121   CGTCAACAGG CGAAGAAACA ACCAACCCAT TCTTCACTGC AGCAGCATTG ACAGTGATCG
  181   CATCTGCAGG CGTACTTGCC CTAAAACGCA AAGAAGAAAA CTAAGTCCAA CCCACACTAT
  241   TTTTTCTAGC CCAAGAAAAA AACAAAAAAA GAGGAAGCCC CTTCCTCTTT TTTTGAACGA
  301   TTGGAAAGCA AAAAGGTCAA AAAGGTACTA AAGTCCCAAA ACCTGGTCT  TTACCTTTTG
  361   CCGCTTATTC TTTAGAATAG AATTATTAGA GAGAAGTCTT AGAAAAATGA GGCTAATTCC
  421   CTAAAGATGA AAAAATAAGG AGCAAATAAT GGCTAGAAAA GATACGAATA ACAGTATTC
  481   GCTTAGAAAA TTAAAAACAG GTACAGCATC AGTAGCGGTC GCTGTGGCTG TTTTAGGAGC
  541   AGGCTTTGCA AACCAAACAA CAGTTAAGGC GGAGTCATCA AATAATGCGG AGTCATCAAA
  601   CATTTCTCAA GAAAGCAAAC TAATAAATAC ATTGACTGAT GAAAATGAGA AACTCAGAGA
  661   AGAGCTCCAA CAGTATTATG CATTAAGTGA TGCTAAAGAA GAAGAACCTA GGTATAAAGC
  721   ATTGAGAGGC GAAAATCAAG ATCTTCGGGA AAAAGAAAGA AAATACCAGG ATAAAATAAA
  781   AAAATTAGAA GAAAAAGAGA AAAACCTAGA AAAAAAATCA GAAGATGTAG AACGTCACTA
  841   TCTTAAAAAA CTAGATCAAG AACATAAAGA ACAACAAGAA CGTCAAAAAA ATCTAGAGGA
  901   ACTCGAACGT CAAAGTCAAC GAGAAATAGA CAAGCGTTAT CAAGAACAAC TCCAAAAACA
  961   ACAACAATTA GAAACAGAAA AGCAAATCTC AGAAGCTAGT CGTAAGAGCC TAAGTCGTGA
 1021   CCTTGAAGCG TCTCGTGCAG CTAAGAAAAA AGTAGAAGCA GACCTAGCTG CTCTTAATGC
 1081   TGAGCACCAA AAACTCAAAG AGGAAAAACA AATCTCAGAC GCAAGCCGTC AAGGCCTAAG
 1141   CCGTGACCTT GAAGCGTCTC GCGAAGCTAA GAAAAAAGTA GAAGCAGACT TAGCCGAAGC
 1201   AAATAGCAAA CTTCAAGCCC TTGAAAAACT AAACAAAGAG CTTGAAGAAG GTAAGAAATT
 1261   ATCAGAAAAA GAAAAAGCTG AGTTACAAGC AAGACTAGAA GCTGAAGCAA AGCTCTTAA
 1321   AGAGCAATTG GCTAAACAAG CTGAAGAACT TGCAAAACTA AAGGCAACC AAACACCAAA
 1381   CGCTAAAGTA GCCCCACAAG CTAACCGTTC AAGATCAGCA ATGACGCAAC AAAAGAGAAC
 1441   GTTACCGTCA ACAGGCGAAG CAGCTAACCC ATTCTTTACA GCAGCAGCTG CAACAGTGAT
 1501   GGTATCTGCA GGTATGCTTG CTCTAAAACG CAAAGAAGAA AACTAAGCTA TTAGACTGAT
 1561   GCTAAAGCTA AGAGAGAATC AAATGATTCT CTCTTTTTGA GTGGCTAAGT AACTAACAAT
 1621   CTCAGTTAGA CCAAAAAATG GGAATGGTTC AAAAAGCTGG CCTTTACTCC TTTTGATTAA
```

Figure 4 continued

```
1681 CCATATATAA CAAAAACATT AGGGAAATAA TAGTAATATT AAGTTTGTTT CCTCAATAAA
1741 ATCAAGGAGT AGATAATGGC TAGACAACAA ACCAAGAAAA ATTATTCACT ACGGAAACTA
1801 AAAACCGGTA CGGCTTCAGT AGCCGTTGCT TTGACCGTTT TGGGCGCAGG TTTTGCAAAC
1861 CAAACGGAAG TAAGAGCTGA TGAAGCAGTT TCTGGAAAAG TGGAAGTAAA AGAAAGTGAA
1921 AAAGAGACTA AGTATAAGAC GTTGGCCTTA AGAGGTGAAA ATGCTGACCT TAGAAACGTA
1981 AATGCAAAAT ATTTAGAGAA AATTAACGCA GAAGAAGAAA AAAATAAAAA ATTAGAAAAA
2041 GAAAAACAAG AGTTAGAAAA CCAAGCCCTT AACTTTCAAG ATGTAATTGA AACTCAGGAA
2101 AAAGAAAAAG AAGATCTCAA AACAACTTTA GCTAAGGCTA CTAAAGAAAA CGAGATCTCA
2161 GAAGCTAGCC GTAAAGGGTT AAGCCGAGAC TTAGAAGCTT
```

SEQ ID NO: 4 — *Staphylococcus aureus* protein A

```
  1 MEQRITLKEA WDQRNGFIQS LKDDPSQSAN VLGEAQKLND SQAPKADAQQ NNFNKDQQSA
 61 FYEILNMPNL NEAQRNGFIQ SLKDDPSQST NVLGEAKKLN ESQAPKADNN FNKEQQNAFY
121 EILNMPNLNE EQRNGFIQSL KDDPSQSANL LSEAKKLNES QAPKADNKFN KEQQNAFYEI
181 LHLPNLNEEQ RNGFIQSLKD DPSQSANLLA EAKKLNDAQA PKADNKFNKE QQNAFYEILH
241 LPNLTEEQRN GFIQSLKDDP GNSRGSVDLQ ITN
```

SEQ ID NO: 5 — Modified Z-domain IgA1 binding protein

VDNKFNKETIQASQEIRLLPNLNGRQKLAFIHSLLDDPSQSANLLAEAKKLNDAQAPK

SEQ ID NO: 6 - AAF03880

```
  1 DIVMTQSPLS LSVTPGEPAS ISCRSSQSLL RRDGHNDLEW YLQKPGQSPQ PLIYLGSTRA
 61 SGVPDRFSGS GSGTDFTLKI IRVEAEDAGT YYCMQNKQTP LTFGQGTRLE IKRTVAAPSV
121 FIFPPS
```

SEQ ID NO: 7 - P01708

```
 1 QSALTQPRSV SGSPGHSVTI SCIGTSSNVG DYKYVSWYQQ HPGKAPKLII YEVSSRPSGV
61 PDRFSGSKSG NTASLTISGL QAEDEADYYC CSYIGSYVFG TGTKVIVLG
```

SEQ ID NO: 8 - P01773

```
 1 QVQLVESGGG VVQAGTSLRL SCTASAFNLS DYAMHWVRQA PGKGLZWVAL ISYGGSBTYY
61 ADSVRGRFTI SRBISKBTLY LZMKTLRTED TAVYYCAKLI AVAGTRBFWG QGTLVTVSL
```

Figure 4 continued

SEQ ID NO: 9 – IgA1 C-region

```
  1  ASPTSPKVFP  LSLCSTQPDG  NVVIACLVQG  FFPQEPLSVT  WSESGQGVTA  RNFPPSQDAS
 61  GDLYTTSSQL  TLPATQCLAG  KSVTCHVKHY  TNPSQDVTVP  CPVPSTPPTP  SPSTPPTPSP
121  SCCHPRLSLH  RPALEDLLLG  SEANLTCTLT  GLRDASGVTF  TWTPSSGKSA  VQGPPERDLC
181  GCYSVSSVLP  GCAEPWNHGK  TFTCTAAYPE  SKTPLTATLS  KSGNTFRPEV  HLLPPPSEEL
241  ALNELVTLTC  LARGFSPKDV  LVRWLQGSQE  LPREKYLTWA  SRQEPSQGTT  TFAVTSILRV
301  AAEDWKKGDT  FSCMVGHEAL  PLAFTQKTID  RLAGKPTHVN  VSVVMAEVDG  TCY
```

SEQ ID NO: 10 – IgA1 hinge region

TVPCPVPSTPPTPSPSTPPTPSPSC

SEQ ID NO: 11 – IgA1 J-chain

```
  1  MKNHLLFWGV  LAVFIKAVHV  KAQEDERIVL  VDNKCKCARI  TSRIIRSSED  PNEDIVERNI
 61  RIIVPLNNRE  NISDPTSPLR  TRFVYHLSDL  CKKCDPTEVE  LDNQIVTATQ  SNICDEDSAT
121  ETCYTYDRNK  CYTAVVPLVY  GGETKMVETA  LTPDACYPD
```

SEQ ID NO: 12 – hinge region fragment

TPPTPSPSTPPTPSPS

SEQ ID NO: 13

TPPTPS

US 8,440,191 B2

CLEARANCE OF ABNORMAL IGA1 IN IGA1 DEPOSITION DISEASES

CROSS-REFERENCE TO RELATED APPLICATIONS

This application is the National Stage of International Application No. PCT/US06/044844, filed Nov. 17, 2006, which claims the benefit of provisional Application No. 60/737,984, filed Nov. 18, 2005.

SEQUENCE LISTING

In accordance with 37 CFR§1.52(e)(5), the present specification makes reference to a Sequence Listing (submitted electronically as a .txt file on May 6, 2009). The .txt file was generated on May 6, 2009 and is 18 kb in size. The entire contents of the Sequence Listing are herein incorporated by reference.

BACKGROUND

Immunoglobulin A1 (IgA1) deposition in human tissues and organs is a characteristic of several human diseases which include, but are not limited to, IgA nephropathy, dermatitis herpetiformis (DH), and Henoch-Schoenlein purpura (HSP). The IgA1 deposits are responsible for a variety of clinical manifestations such as renal failure, skin blistering, rash, arthritis, gastrointestinal bleeding and abdominal pain.

There are several available treatment options for patients that present with abnormal IgA1 deposition. These include administration of corticosteroids that have immunosuppressive and anti-inflammatory properties, dietary fish oil supplements that reduce renal inflammation, angiotensin converting enzyme inhibitors that reduce the risk of progressive renal disease and renal failure, and dapsone, a drug used to treat DH. DH can also be treated by gluten-free diet, as this disorder often is accompanied by gluten sensitive enteropathy. Such treatments do not directly act on IgA1 deposits in tissue or organs.

Human immunoglobulin A (IgA) synthesis exceeds the combined total of all the other immunoglobulin classes (Rifai et al. J. Exp. Med. 191:12, Jun. 19, 2000 2171-2181). It is estimated that 66 mg of IgA/kg of body weight is produced every day, compared with 34 mg of IgG and 7.9 mg of IgM. There are two isotypes of IgA, IgA1 and IgA2. On mucosal surfaces (gut, respiratory tract, genital track, etc) both IgA1 and IgA2 are present, synthesized by local B cells. In the blood, however, IgA1 predominates, and its origin is B cells in the bone marrow, lymph nodes, and spleen (James V. Donadio, M. D., and Joseph P. Grande, M. D., PHD. N Engl J Med, Vol. 347, No. 10: 738-748. Sep. 5, 2002).

The main differences between the IgA1 and IgA2 isotypes lie in the hinge region of the heavy polypeptide chain; a 13-amino acid deletion characterizes the IgA2 hinge region. This segment in IgA1 contains several Ser and Thr amino acid residues that are O-glycosylated, but the absence of this segment in IgA2 results in IgA2 having no O-linked oligosaccharides. IgA1 also has two N-linked carbohydrates in the CH2 domain at residue Asn263, and in the CH3 domain at Asn459. All IgA2 allotypes have two additional N-linked sites, in the CH1 domain at Asn166 and in the CH2 domain at Asn337. The IgA2m(2) and the IgA2(n) allotypes have a fifth N-linked site in the CH1 domain, at Asn211. N-linked glycans are complex structures attached to specific asparagine residues and are common on circulating proteins. In contrast, O-glycans as in the IgA1 hinge consist of simple sugar chains connected to serine or threonine residues, and while abundant on all-surface proteins, they are uncommon on circulating proteins. In IgA1 each O-glycan has a core N-acetyl galactosamine (GalNAc) unit in O-linkage with serine or threonine, and the chain may be extended by the sequential addition of galactose (Gal) in β1,3 linkage with GalNAc, and with one or two sialic units in 2,3 linkage with Gal or 2,6 linkage with GalNAc (Alice C. Allen et al. J Am Soc Nephrol 10: 1763-1771, 1999; Taj S. Mattu et al., J. Bio. Chem. 1998, 273:4:2260-72). Thus, each O-glycan may consist of one of four different forms. These O-glycans are identical to those displayed by membrane-bound proteins such as mucins.

Several recent studies have implicated O-glycosylation defects in IgA1 as being involved in the pathogenesis of IgA deposition diseases (Alice Allen et al., J Am Soc Nephrol 10: 1763-1771, 1999; Mestecky J, Tomana et al., Contrib Nephrol 1993; 104:172-82; Milan Tomana et al., The J Clin Invest, July 1999, Volume 104, Number 1, 73-81; Tomana M, Matousovic et al., Kidney Int 1997; 52:509-16; Allen A C et al., Mesangial IgA1 in IgA nephropathy exhibits aberrant O-glycosylation: observations in three patients. Kidney (Abstract) Int 2001; 60:969-73.

As indicated earlier, it has been proposed that the lack of galactose residue could substantially reduce serum IgA1 clearance; that is, it keeps this form of IgA in the circulation for a longer time than normal. The mechanism behind failure of IgA1 proteins to acquire normal amounts and form of O-linked glycans are unknown.

SUMMARY OF THE INVENTION

The present invention relates to isolated IgA1 binding proteins which have been modified to comprise O- or N-linked glycan molecules, and further relates to methods for decreasing the amount of IgA1 in an individual by administering such a modified IgA1 binding protein. Based on the binding of the specific glycan-modified IgA1 binding proteins described herein, the invention also relates to a method for screening for additional IgA1 binding proteins which may be modified by the addition of O- or N-linked glycans, thus making them useful for decreasing the amount of IgA1 in an individual.

The invention encompasses an isolated antibody polypeptide which specifically binds IgA1, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the antibody polypeptide is selected from the group consisting of a dAb, a Fab, an scFv, an Fv, or a disulfide-bonded Fv.

In one embodiment, the Fab is of human origin.

In one embodiment, the Fab is a fragment of a humanized chimeric monoclonal IgG.

In one embodiment, the antibody polypeptide binds to the hinge region of IgA1.

In one embodiment, the antibody polypeptide binds to the $CH_2$—$CH_3$ region interface of IgA1.

In one embodiment, the isolated antibody polypeptide specifically binds an IgA1 hinge region having the sequence TPPTPSPSTPPTPSPS (SEQ ID NO:12).

In one embodiment, the isolated antibody polypeptide specifically binds to GalNAc residues on the hinge region.

In one embodiment, the isolated antibody polypeptide binds to the J chain of a dimeric IgA.

In one embodiment, the O-linked glycan has the following formula:

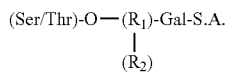

wherein, (Ser/Thr) is one of the one or more non-naturally occurring serine or threonine residues which has been modified by the addition of the O-linked glycan;
wherein S.A. is a sialic acid;
wherein, $R_1$ is H, $(GalNAc)_n$, where n=1, 2, 3, 4, 5, 6, 7, 8, 9, or 10;
and wherein $R_2$ is H or S.A.

In one embodiment, the N-linked glycan has the following formula:

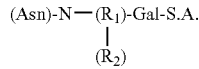

wherein (Asn) is one of the one or more non-naturally occurring asparagine residues which has been modified by the addition of the N-linked glycan;
wherein S.A. is a sialic acid;
wherein, $R_1$ is H, $(GlcNAc)_n$, where n=1, 2, 3, 4, 5, 6, 7, 8, 9, or 10;
and wherein $R_2$ is H or S.A.

In a further embodiment, the N-linked glycan is a biantennary structure having the formula:

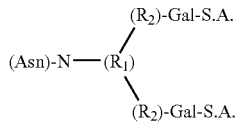

wherein (Asn) is one of the one or more non-naturally occurring asparagine residues which has been modified by the addition of the N-linked glycan;
wherein S.A. is a sialic acid;
wherein $R_1$ is H, $(GlcNAc)_n$, or $(GlcNAc)_n$ linked to mannose, wherein n=1, 2, 3, 4, 5, 6, 7, 8, 9, or 10;
wherein $R_2$ is H, mannose, $(GlcNAc)_n$, or mannose linked to $(GlcNAc)_n$, wherein n=1, 2, 3, 4, 5, 6, 7, 8, 9, or 10.

The invention also encompasses an isolated polypeptide comprising the *Streptococcus pyogenes* protein Sir22, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the O-linked glycan has the following formula:

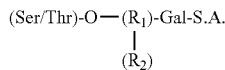

wherein, (Ser/Thr) is one of the one or more non-naturally occurring serine or threonine residues which has been modified by the addition of the O-linked glycan;
wherein S.A. is a sialic acid;
wherein, $R_1$ is H, $(GalNAc)_n$, where n=1, 2, 3, 4, 5, 6, 7, 8, 9, or 10;
and wherein $R_2$ is H or S.A.

In one embodiment, the N-linked glycan has the following formula:

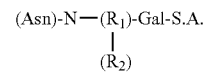

wherein (Asn) is one of the one or more non-naturally occurring asparagine residues which has been modified by the addition of the N-linked glycan;
wherein S.A. is a sialic acid;
wherein, $R_1$ is H, $(GlcNAc)_n$, where n=1, 2, 3, 4, 5, 6, 7, 8, 9, or 10;
and wherein $R_2$ is H or S.A.

In a further embodiment, the N-linked glycan is a biantennary structure having the formula:

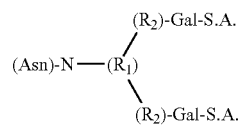

wherein (Asn) is one of the one or more non-naturally occurring asparagine residues which has been modified by the addition of the N-linked glycan;
wherein S.A. is a sialic acid;
wherein $R_1$ is H, $(GlcNAc)_n$, or $(GlcNAc)_n$ linked to mannose, wherein n=1, 2, 3, 4, 5, 6, 7, 8, 9, or 10;
wherein $R_2$ is H, mannose, $(GlcNAc)_n$, or mannose linked to $(GlcNAc)_n$, wherein n=1, 2, 3, 4, 5, 6, 7, 8, 9, or 10.

In one embodiment, the *Streptococcus pyogenes* protein Sir22 comprises the sequence of SEQ ID NO: 2.

The invention also encompasses an isolated *Staphylococcus aureus* protein A modified Z domain polypeptide that binds to IgA1, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the O-linked glycan has the following formula:

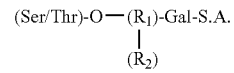

wherein, (Ser/Thr) is one of the one or more non-naturally occurring serine or threonine residues which has been modified by the addition of the O-linked glycan;
wherein S.A. is a sialic acid;
wherein, $R_1$ is H, $(GalNAc)_n$, where n=1, 2, 3, 4, 5, 6, 7, 8, 9, or 10;
and wherein $R_2$ is H or S.A.

In one embodiment, the N-linked glycan has the following formula:

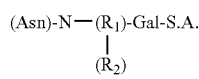

wherein (Asn) is one of the one or more non-naturally occurring asparagine residues which has been modified by the addition of the N-linked glycan;
wherein S.A. is a sialic acid;
wherein, $R_1$ is H, $(GlcNAc)_n$, where n=1, 2, 3, 4, 5, 6, 7, 8, 9, or 10;
and wherein $R_2$ is H or S.A.

In a further embodiment, the N-linked glycan is a biantennary structure having the formula:

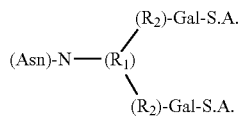

wherein (Asn) is one of the one or more non-naturally occurring asparagine residues which has been modified by the addition of the N-linked glycan;
wherein S.A. is a sialic acid;
wherein $R_1$ is H, $(GlcNAc)_n$, or $(GlcNAc)_n$ linked to mannose, wherein n=1, 2, 3, 4, 5, 6, 7, 8, 9, or 10;
wherein $R_2$ is H, mannose, $(GlcNAc)_n$, or mannose linked to $(GlcNAc)_n$, wherein n=1, 2, 3, 4, 5, 6, 7, 8, 9, or 10.

In one embodiment, the *Staphlococcus aureus* protein comprises the sequence of SEQ ID NO: 5.

The invention also encompasses, an isolated IgA1 binding polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan, wherein the IgA1 binding polypeptide is selected from the group consisting of CD89, polymeric Ig receptor, transferrin receptor, asialoglycoprotein receptor, and Fcα/μR.

In one embodiment, the O-linked glycan has the following formula:

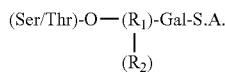

wherein, (Ser/Thr) is one of the one or more non-naturally occurring serine or threonine residues which has been modified by the addition of the O-linked glycan;
wherein S.A. is a sialic acid;
wherein, $R_1$ is H, $(GalNAc)_n$, where n=1, 2, 3, 4, 5, 6, 7, 8, 9, or 10;
and wherein $R_2$ is H or S.A.

In one embodiment, the N-linked glycan has the following formula:

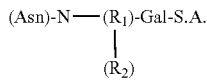

wherein (Asn) is one of the one or more non-naturally occurring asparagine residues which has been modified by the addition of the N-linked glycan;
wherein S.A. is a sialic acid;
wherein, $R_1$ is H, $(GlcNAc)_n$, where n=1, 2, 3, 4, 5, 6, 7, 8, 9, or 10;
and wherein $R_2$ is H or S.A.

In a further embodiment, the N-linked glycan is a biantennary structure having the formula:

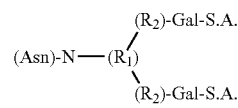

wherein (Asn) is one of the one or more non-naturally occurring asparagine residues which has been modified by the addition of the N-linked glycan;
wherein S.A. is a sialic acid;
wherein $R_1$ is H, $(GlcNAc)_n$, or $(GlcNAc)_n$ linked to mannose, wherein n=1, 2, 3, 4, 5, 6, 7, 8, 9, or 10;
wherein $R_2$ is H, mannose, $(GlcNAc)_n$, or mannose linked to $(GlcNAc)_n$, wherein n=1, 2, 3, 4, 5, 6, 7, 8, 9, or 10.

The invention encompasses a method of reducing the amount of IgA1 in an individual, comprising administering to the individual an isolated antibody polypeptide which binds to IgA1, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the IgA1 is abnormally glycosylated.

In one embodiment, the antibody polypeptide is selected from the group consisting of a dAb, a Fab, an scFv, an Fv, or a disulfide-bonded Fv.

In one embodiment, the Fab is of human origin.

In one embodiment, the Fab is a fragment of a humanized chimeric monoclonal IgG.

In one embodiment, the antibody polypeptide binds to the hinge region of IgA1.

In one embodiment, the antibody polypeptide binds to the $CH_2$—$CH_3$ region interface of IgA1.

In one embodiment, the isolated antibody polypeptide specifically binds an IgA1 hinge region having the sequence TPPTPSPSTPPTPSPS (SEQ ID NO:12).

In one embodiment, the isolated antibody polypeptide specifically binds to GalNAc residues on the hinge region.

In one embodiment, the isolated antibody polypeptide binds to the J chain of a dimeric IgA.

In one embodiment, the O-linked glycan has the following formula:

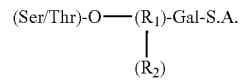

wherein, (Ser/Thr) is one of the one or more non-naturally occurring serine or threonine residues which has been modified by the addition of the O-linked glycan;
wherein S.A. is a sialic acid;
wherein, $R_1$ is H, $(GalNAc)_n$, where n=1, 2, 3, 4, 5, 6, 7, 8, 9, or 10;
and wherein $R_2$ is H or S.A.

In one embodiment, the N-linked glycan has the following formula:

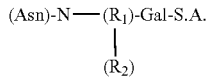

wherein (Asn) is one of the one or more non-naturally occurring asparagine residues which has been modified by the addition of the N-linked glycan;

wherein S.A. is a sialic acid;

wherein, $R_1$ is H, $(GlcNAc)_n$, where n=1, 2, 3, 4, 5, 6, 7, 8, 9, or 10;

and wherein $R_2$ is H or S.A.

In a further embodiment, the N-linked glycan is a biantennary structure having the formula:

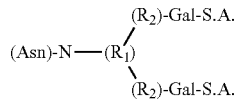

wherein (Asn) is one of the one or more non-naturally occurring asparagine residues which has been modified by the addition of the N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

and wherein $R_2$ is H, mannose, $(GlcNAc)_n$, or mannose linked to $(GlcNAc)_n$, wherein n=1, 2, 3, 4, 5, 6, 7, 8, 9, or 10.

The invention also encompasses a method for decreasing the amount of IgA1 in an individual comprising administering to the individual an isolated polypeptide comprising the *Streptococcus pyogenes* protein Sir22, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the IgA1 is abnormally glycosylated.

In one embodiment, the O-linked glycan has the following formula:

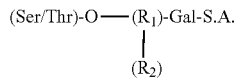

wherein, (Ser/Thr) is one of the one or more non-naturally occurring serine or threonine residues which has been modified by the addition of the O-linked glycan;

wherein S.A. is a sialic acid;

wherein, $R_1$ is H, $(GalNAc)_n$, where n=1, 2, 3, 4, 5, 6, 7, 8, 9, or 10;

and wherein $R_2$ is H or S.A.

In one embodiment, the N-linked glycan has the following formula:

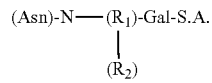

wherein (Asn) is one of the one or more non-naturally occurring asparagine residues which has been modified by the addition of the N-linked glycan;

wherein S.A. is a sialic acid;

wherein, $R_1$ is H, $(GlcNAc)_n$, where n=1, 2, 3, 4, 5, 6, 7, 8, 9, or 10;

and wherein $R_2$ is H or S.A.

In a further embodiment, the N-linked glycan is a biantennary structure having the formula:

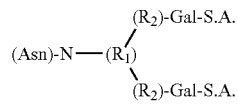

wherein (Asn) is one of the one or more non-naturally occurring asparagine residues which has been modified by the addition of the N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

wherein $R_2$ is H, mannose, $(GlcNAc)_n$, or mannose linked to $(GlcNAc)_n$, wherein n=1, 2, 3, 4, 5, 6, 7, 8, 9, or 10.

In one embodiment, the *Streptococcus pyogenes* protein Sir22 comprises the sequence of SEQ ID NO: 2.

The invention also encompasses method for treatment of a disease characterized by IgA1 deposition, comprising administering to an individual in need thereof, an isolated antibody polypeptide which binds to IgA1, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the antibody polypeptide is selected from the group consisting of a dAb, a Fab, an scFv, an Fv, or a disulfide-bonded Fv.

In one embodiment, the Fab is of human origin.

In one embodiment, the Fab is a fragment of a humanized chimeric monoclonal IgG.

In one embodiment, the antibody polypeptide binds to the hinge region of IgA1.

In one embodiment, the antibody polypeptide binds to the $CH_2$—$CH_3$ region interface of IgA1.

In one embodiment, the isolated antibody polypeptide specifically binds an IgA1 hinge region having the sequence TPPTPSPSTPPTPSPS (SEQ ID NO:12).

In one embodiment, the isolated antibody polypeptide specifically binds to GalNAc residues on the hinge region.

In one embodiment, the isolated antibody polypeptide binds to the J chain of a dimeric IgA.

In one embodiment, the O-linked glycan has the following formula:

$$(Ser/Thr)\text{-}O—(R_1)\text{-}Gal\text{-}S.A.$$
$$|$$
$$(R_2)$$

wherein, (Ser/Thr) is one of the one or more non-naturally occurring serine or threonine residues which has been modified by the addition of the O-linked glycan;

wherein S.A. is a sialic acid;

wherein, $R_1$ is H, $(GalNAc)_n$, where n=1, 2, 3, 4, 5, 6, 7, 8, 9, or 10;

and wherein $R_2$ is H or S.A.

In one embodiment, the N-linked glycan has the following formula:

$$(Asn)\text{-}N—(R_1)\text{-}Gal\text{-}S.A.$$
$$|$$
$$(R_2)$$

wherein (Asn) is one of the one or more non-naturally occurring asparagine residues which has been modified by the addition of the N-linked glycan;

wherein S.A. is a sialic acid;

wherein, $R_1$ is H, $(GlcNAc)_n$, where n=1, 2, 3, 4, 5, 6, 7, 8, 9, or 10;

and wherein $R_2$ is H or S.A.

In a further embodiment, the N-linked glycan is a biantennary structure having the formula:

$$(Asn)\text{-}N—(R_1) \begin{array}{c} (R_2)\text{-}Gal\text{-}S.A. \\ \diagup \\ \diagdown \\ (R_2)\text{-}Gal\text{-}S.A. \end{array}$$

wherein (Asn) is one of the one or more non-naturally occurring asparagine residues which has been modified by the addition of the N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

and wherein $R_2$ is H, mannose, $(GlcNAc)_n$, or mannose linked to $(GlcNAc)_n$, wherein n=1, 2, 3, 4, 5, 6, 7, 8, 9, or 10.

The invention further encompasses a method for treatment of a disease characterized by IgA1 deposition comprising administering to an individual in need thereof, an isolated polypeptide comprising the *Streptococcus pyogenes* protein Sir22, the polypeptide comprising one or both of (a) a naturally occurring or non-naturally occurring serine or threonine residue that has been artificially modified by the addition of an O-linked glycan, and (b) a naturally occurring or non-naturally occurring asparagine residue that has been artificially modified by the addition of an N-linked glycan.

In one embodiment, the O-linked glycan has the following formula:

$$(Ser/Thr)\text{-}O—(R_1)\text{-}Gal\text{-}S.A.$$
$$|$$
$$(R_2)$$

wherein, (Ser/Thr) is one of the one or more non-naturally occurring serine or threonine residues which has been modified by the addition of the O-linked glycan;

wherein S.A. is a sialic acid;

wherein, $R_1$ is H, $(GalNAc)_n$, where n=1, 2, 3, 4, 5, 6, 7, 8, 9, or 10;

and wherein $R_2$ is H or S.A.

In one embodiment, the N-linked glycan has the following formula:

$$(Asn)\text{-}N—(R_1)\text{-}Gal\text{-}S.A.$$
$$|$$
$$(R_2)$$

wherein (Asn) is one of the one or more non-naturally occurring asparagine residues which has been modified by the addition of the N-linked glycan;

wherein S.A. is a sialic acid;

wherein, $R_1$ is H, $(GlcNAc)_n$, where n=1, 2, 3, 4, 5, 6, 7, 8, 9, or 10;

and wherein $R_2$ is H or S.A.

In a further embodiment, the N-linked glycan is a biantennary structure having the formula:

$$(Asn)\text{-}N—(R_1) \begin{array}{c} (R_2)\text{-}Gal\text{-}S.A. \\ \diagup \\ \diagdown \\ (R_2)\text{-}Gal\text{-}S.A. \end{array}$$

wherein (Asn) is one of the one or more non-naturally occurring asparagine residues which has been modified by the addition of the N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

wherein $R_2$ is H, mannose, $(GlcNAc)_n$, or mannose linked to $(GlcNAc)_n$, wherein n=1, 2, 3, 4, 5, 6, 7, 8, 9, or 10.

In one embodiment, the *Streptococcus pyogenes* protein Sir22 comprises the sequence of SEQ ID NO: 2.

BRIEF DESCRIPTION OF THE FIGURES

FIG. 3 shows a schematic of a humanized antibody. A chimeric antibody is shown on the left and a fully reshaped antibody on the right. In the chimeric antibody the rodent heavy and light chain variable regions (white) are attached to human constant regions (black). After full reshaping the four framework regions within each V region are humanized, leaving only the six complementarity determining regions (CDR), three in the heavy and three in the light chains.

FIG. 4 shows the amino acid and nucleic acid sequences of the invention.

DETAILED DESCRIPTION

Figure 1:
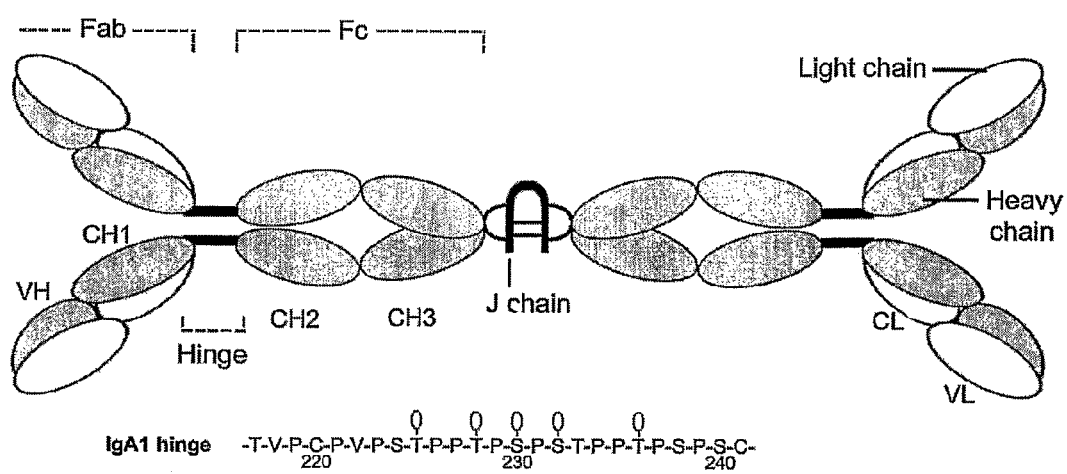
FIG. 1 shows a schematic structure of dimeric IgA1, including the sequence of the hinge region (SEQ ID NO: 10).

Without being bound to one particular theory, based on observations that abnormal IgA1 lacking the correct glycosylation patterns is observed in IgA1 deposition diseases, potentially causing a reduction in serum IgA1 clearance, the present invention describes a method for modification of IgA in a way that will promote its clearance from the circulation, or that will reduce its capacity to cause inflammatory injury at tissue deposition sites. The present invention is thus based in part on the discovery that proteins which bind to IgA1 and which have been modified to include one or more O- or N-linked glycan molecules may be useful to promote clearance of IgA1 from the circulation, and thus aid in the prevention and/or treatment of IgA1 deposition diseases. In one embodiment, an O-linked glycan is linked to one or more serine or threonine residues which have been added to the IgA1 binding protein. In a further embodiment an N-linked glycan is linked to one or more asparagine residues that have been added to the IgA1 binding protein.

As used herein, the term "IgA1" refers to a subclass of the IgA immunoglobulin isotype. "IgA1" as used herein refers to a whole IgA1 immunoglobulin and also refers to fragments of a whole IgA1 immunoglobulin, including, but not limited to Fc, Fab, F(ab')2, Fab', Fv, dAbs and single chain antibodies (scFv) containing a IgA1 $V_L$ and $V_H$ domain joined by a peptide linker. Thus, a peptide which binds to IgA1 according to the invention, can bind to either the intact IgA1 immunoglobulin, or fragments thereof.

As used herein, the term "specifically binds" refers to the interaction of two molecules, e.g., a ligand and a protein or peptide, wherein the interaction is dependent upon the presence of particular structures on the respective molecules. For example, when the two molecules are protein molecules, a structure on the first molecule recognizes and binds to a structure on the second molecule, rather than to proteins in general. "Specific binding", as the term is used herein, means that a molecule binds its specific binding partner with at least 2-fold greater affinity, and preferably at least 10-fold, 20-fold, 50-fold, 100-fold or higher affinity than it binds a non-specific molecule. Alternatively, "specifically binds" as used herein refers to the binding of two protein molecules to each other with a dissociation constant ($K_d$) of 1 μM or lower. For example, the affinity or $K_d$ for a specific binding interaction can be about 1 μM, or lower, about 500 nM or lower, and about 300 nM or lower. Preferably the $K_d$ for a specific binding interaction is about 300 nM or lower. Specific binding between two molecules (e.g., protein molecules) can be measured using methods known in the art. For example, specific binding may be determined as measured by surface plasmon resonance analysis using, for example, a BIAcore™ surface plasmon resonance system and BIAcore™ kinetic evaluation software (e.g., version 2.1).

Accordingly, an "isolated polypeptide which specifically binds to IgA1" or "IgA1 binding protein" is a polypeptide which binds, according to the parameters outlined in the preceding paragraph, to IgA1 to the substantial exclusion of any other immunoglobulin molecule, wherein "substantial exclusion" is defined as being "specific binding" as described above.

As used herein, an "O-linked glycan" refers to a polymer comprising a plurality (e.g., two or more) of monosaccharide residues joined to each other by glycosidic linkages, wherein the polymer comprises at least one galactose residue which is linked (directly or indirectly) to the hydroxyl group of an amino acid side chain. The galactose is further linked optionally to a sialic acid (S.A.) molecule. An O-linked glycan of the invention preferably has the following structure:

wherein, (Ser/Thr) is one or more non-naturally occurring serine or threonine residues which has been introduced into an IgA1 binding protein and modified by the addition of the O-linked glycan;

wherein S.A. is a sialic acid;

wherein, $R_1$ is H, $(GalNAc)_n$, where n=1, 2, 3, 4, 5, 6, 7, 8, 9, or 10;

and wherein when $R_1$ is $(GalNAc)_n$, $R_2$ is S.A.

As used herein, "N-linked glycan" refers to a glycan attached to a protein through the side chain (amide) nitrogen of asparagine. An N-linked glycan of the invention preferably has the following structure:

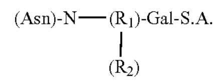

wherein (Asn) is one or more non-naturally occurring asparagine residues which has been modified by the addition of said N-linked glycan;

wherein S.A. is a sialic acid;

wherein, $R_1$ is H, or $(GlcNAc)_n$, where n=1, 2, 3, 4, 5, 6, 7, 8, 9, or 10;

and wherein when $R_1$ is (GlcNAc), $R_2$ is H, or S.A.

As used herein, an N-linked glycan can also refer to a branched glycan having the following structure:

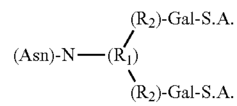

wherein (Asn) is one or more non-naturally occurring asparagine residues which has been modified by the addition of said N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

wherein $R_2$ is H, mannose, $(GlcNAc)_n$, or mannose linked to $(GlcNAc)_n$, wherein n=1, 2, 3, 4, 5, 6, 7, 8, 9, or 10.

In addition, an "N-linked glycan" can refer to a branched glycan with more than the two branches shown above, but which has three, four and up to five or more branches. For example, the base chain (Asn)-N—($R_1$) may be linked to three, four, and up to five or more ($R_2$)-Gal-S.A. branches, wherein the $R_1$ and $R_2$ moieties are defined as described above.

As used herein, the term "isolated" in the context of an isolated IgA1 or isolated IgA1 binding protein (e.g., antibody polypeptide) refers to a population of molecules, e.g., polypeptides or polynucleotides, the composition of which comprises less than 50% (by weight), preferably less than 40% and most preferably 2% or less, contaminating molecules of an unlike nature. Examples of non-limiting methods of isolation include the isolation of an IgA1 or IgA1 binding protein that has a poly-Histidine tag using a metal-chelate resin or beads, immunoprecipitation, and affinity column purification using anti-tag antibodies.

As used herein, the term "antibody polypeptide" refers to an immunoglobulin molecule, or fragment thereof, that is capable of binding antigen, such as IgA1. The term "antibody polypeptide" is preferably not intended to include whole antibodies, e.g., of any isotype (IgG, IgA, IgM, IgE, etc), but to include fragments thereof which are specifically reactive with IgA1 protein. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fc, Fab, F(ab')2, Fab', Fv, dAbs and single chain antibodies (scFv) containing a $V_L$ and $V_H$ domain joined by a peptide linker. The scFv's may be covalently or non-covalently linked to form antibodies having two or more binding sites. Thus, antibody polypeptides include polyclonal, monoclonal, or other purified preparations of antibody polypeptides and recombinant antibody polypeptides.

As used herein, "naturally occurring or non-naturally occurring serine or threonine residue" and/or "naturally occurring or non-naturally occurring asparagine residue" refers to a serine, threonine, or asparagine residue, respectively, which exists in a peptide (e.g., an IgA1 binding polypeptide) in nature without human intervention (naturally occurring), or refers to a serine, threonine, or asparagine residue, respectively, which has been inserted through human intervention (non-naturally occurring) into a polypeptide (e.g., an IgA1 binding polypeptide).

As used herein, "artificially modified" refers to the modification of an amino acid residue of a peptide by human intervention or manipulation to link the residue to an O- or N-linked glycan.

As used herein, the term "IgA1 deposition" refers to the accumulation of IgA1 immunoglobulin in aggregated or non-aggregated form in human tissue or organs.

Herein, a "disease characterized by IgA1 deposition" refers to any disease in which IgA1 deposition occurs, such as, but not limited to IgA nephropathy, dermatitis herpetiformis, and Henoch-Schoenlein purpura.

As used herein, "IgA nephropathy" refers to a kidney disease characterized by IgA1 deposits in the kidney and preferably in the renal mesangium.

As used herein, "dermatitis herpetiformis" refers to a chronic blistering disease associated with deposits of IgA1 in skin and other tissues.

As used herein, "Henoch-Schoenlein purpura" refers to a systemic vasculitis and kidney disease characterized by deposition of IgA1 in blood vessel walls and renal mesangium.

As used herein, a "pharmaceutical composition" comprises a pharmacologically effective amount of an active agent and a pharmaceutically acceptable carrier. As used herein, "pharmacologically effective amount," or simply "effective amount" refers to that amount of an agent effective to produce the intended pharmacological, therapeutic or preventive result. For example, if a given clinical treatment is considered effective when there is at least a 25% reduction in a measurable parameter associated with a disease or disorder.

As used herein, the term "human antibody polypeptide" refers to an antibody polypeptide which specifically binds to IgA1, and which has a sequence derived from a human immunoglobulin. A sequence is "derived from" a human immunoglobulin coding sequence when the sequence is either: a) isolated from a human individual or from cells or a cell line from a human individual; b) isolated from a library of cloned human antibody gene sequences (or a library of human antibody V domain sequences); c) when a cloned human antibody gene sequence (or a cloned human V region sequence (including, e.g., a germline V gene segment)) was used to generate one or more diversified sequences that were then selected for binding to a desired target antigen; or d) isolated from a transgenic animal (e.g., rodent) which has been modified to express human antibody genes, such that the transgenic animal will generate human antibodies against a foreign antigen.

As used herein, "humanized antibody polypeptide" refers to an antibody polypeptide, as defined herein, in which the light and/or heavy chain V region complementarity determining regions (CDRs) are of animal origin (e.g., rodent), but which has been modified to replace constant region and/or variable region framework sequences with sequences of human origin, while retaining the original antigen binding specificity.

As used herein, "treatment" refers to a reduction of abnormal IgA1 in the circulation to prevent it to be deposited in tissues including kidney and skin of at least about 5% in response to the administration of an isolated polypeptide of the invention compared to the amount of IgA1 in the circulation in the same individual prior to administration of the isolated polypeptide of the invention. For example, "treatment" can refer to a increase in IgA1 clearance of at least about 5%, 10%, 15%, 20%, 25%, 30%, 35%, 40%, 45%, 50%, 55%, 60%, 65%, 70%, 75%, 80%, 85%, 90%, 95% and up to and including at least about 100% relative to the amount of IgA1 in the circulation measured in the same individual prior to the administration of the isolated polypeptide of the invention. In addition, "treatment" can refer to a decrease in IgA1 deposition of at least about 5%, 10%, 15%, 20%, 25%, 30%, 35%, 40%, 45%, 50%, 55%, 60%, 65%, 70%, 75%, 80%, 85%, 90%, 95% and up to and including at least about 100% relative to the amount of IgA1 deposition in a control individual not administered the polypeptide of the invention. Preferably, treatment refers to a increase in IgA1 clearance of at least about 25% relative to the amount of IgA1 in the circulation in the same individual prior to administration of the isolated polypeptide of the invention.

As used herein, a "therapeutically effective amount" means the total amount of each active component of the pharmaceutical composition or method that is sufficient to show a meaningful patient benefit, i.e., treatment, healing, arrest of progression, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. Generally, a composition will be administered in a single dose in the range of 100 µg-10 mg/kg body weight, preferably in the range of 1 µg-100 µg/kg body weight. This dosage may be repeated daily, weekly, monthly, yearly, or as considered appropriate by the treating physician.

When a therapeutically effective amount of the therapeutic agent of the present invention is administered orally, the composition of the present invention can be in the form of a liquid, the composition contains from about 0.5 to 90% by weight of protein of the present invention, and preferably from about 1 to 50% protein of the present invention.

As used herein, "reduce" refers to a decrease in the amount of abnormally glycosylated IgA1 measurable in the blood, plasma, lymph, or other tissue by at least about 5%. For example, "reduce" refers to a decrease in measurable abnormally glycosylated IgA1 by at least about 5%, 10%, 20%, 30%, 40%, 50%, 60%, 70%, 80%, 90%, and up to and including about 100%. As used herein, "reduce" can refer to a reduction in circulating IgA1 and/or IgA1 present in tissues.

As used herein, "circulating IgA1" refers to the amount of measurable IgA1 present in the blood, serum, plasma, or lymph of an individual.

As used herein, "abnormally glycosylated IgA1" refers to an IgA1 which lacks at least one O- or N-linked glycan molecule which is normally linked to IgA1. For example, an abnormally glycosylated IgA1 molecule may refer to IgA1 which lacks at least one O-linked glycan linked to a serine or threonine residue present in the hinge region, or which lacks at least one N-linked carbohydrates in the CH2 domain at residue Asn263, or in the CH3 domain at Asn459. Alternatively or in addition, an abnormally glycosylated IgA1 can refer to an IgA1 molecule in which one or more of the normally present O- or N-linked glycan molecules lack the terminal Gal-S.A. moiety. That is, for an O-linked glycan of an abnormally glycosylated IgA1, the terminal moiety on a glycan chain would be GalNAc, for example. Where the chain is an N-linked glycan chain of an abnormally glycosylated IgA1, the terminal moiety on the chain would be, for example, GlcNAc.

The present invention provides IgA1 binding proteins which have been artificially modified to comprise one or more serine or threonine residues coupled to an O-linked glycan and/or one or more asparagine residues coupled to a N-linked glycan. The serine, threonine, and or asparagine residues of the IgA1 binding protein may be either naturally occurring in the binding protein, or may be introduced into the binding protein by methods known in the art including, but not limited to, random or site-directed mutagenesis, or direct addition using transferases and other reagents that add oligosaccharides to proteins. The invention also relates to methods for decreasing the amount of IgA1 in an individual by administering to the individual an effective amount of the modified IgA1 binding protein described herein. The invention also encompasses a method for treating a disease characterized by IgA1 deposition by administering to an individual in need thereof, one or more of the modified IgA1 binding proteins described herein. The invention is based in part on the discovery that binding interactions between an O- or N-linked glycan-modified IgA1 binding protein and the galactose deficient IgA1 found in individuals with IgA1 deposition diseases can promote the removal of circulating IgA1, and treatment of the IgA1 deposition disease. IgA1 typically has multiple carbohydrates on the heavy (alpha) polypeptide chains, including approximately five O-linked glycans that are bound to serine or threonine residues in the hinge region, the section between the Fc and Fab domains. In IgA nephropathy and related IgA deposition disorders, it has been observed that the O-linked glycans differ from normal, with the main finding being a lack of galactose residues. The consequence of this defect is that the normal clearance of IgA1 from the circulation is impaired, because clearance depends on galactose (Gal) or N-acetylgalactosamine (GalNAc) recognition by the hepatic asialoglycoprotein receptor (ASGPR). Thus in the absence of these carbohydrate groups, clearance of IgA1 will be delayed, and the current view is that the sustained circulation of underglycosylated IgA1 can result in formation of immune complexes, and tissue deposition. While the exact composition of these complexes is not known, they contain IgA1 as a major constituent. Once in tissue, it is presently thought that the IgA1 Fc domains react with CD89 on myeloid cells to trigger cytokine release, and local inflammation, with the result that tissue is sufficiently damaged to induce change in its function.

IgA1

IgA1 refers to an isotype (sometimes referred to as subclass) of IgA immunoglobulin originating from B cells of the bone marrow, lymph nodes and spleen, and can refer to a whole IgA1 immunoglobulin or to a fragment of a whole IgA1 immunoglobulin, including, but not limited to Fc, Fab, F(ab')2, Fab', Fv, dabs and single chain antibodies (scFv) containing a IgA1 $V_L$ and $V_H$ domain joined by a peptide linker. Thus, a peptide which binds to IgA1 according to the invention, can bind to either the intact IgA1 immunoglobulin, or fragments thereof.

IgA1 typically has multiple carbohydrates on the heavy (alpha) polypeptide chains, including approximately five O-linked glycans that are bound to serine or threonine residues in the hinge region, the section between the Fc and Fab domains. In IgA nephropathy and related IgA deposition disorders, it has been observed that the O-linked glycans differ from normal, with the main finding being a lack of galactose residues. The consequence of this defect is that the normal clearance of IgA1 from the circulation is impaired, because clearance depends on galactose (Gal) or N-acetylgalactosamine (GalNAc) recognition by the hepatic asialoglycoprotein receptor (ASGPR). Thus in the absence of these carbohydrate groups, clearance of IgA1 will be delayed, and the current view is that the sustained circulation of underglycosylated IgA1 can result in formation of immune complexes, and tissue deposition. While the exact composition of these complexes is not known, they contain IgA1 as a major constituent. Once in tissue, it is presently thought that the IgA1 Fc domains react with CD89 on myeloid cells to trigger cytokine release, and local inflammation.

Human immunoglobulin A (IgA) synthesis exceeds the combined total of all the other immunoglobulin classes (Rifai et al. J. Exp. Med. 191:12, Jun. 19, 2000 2171-2181). It is estimated that 66 mg of IgA/kg of body weight is produced every day, compared with 34 mg of IgG and 7.9 mg of IgM. There are two isotype of IgA, IgA1 and IgA2. On mucosal surfaces (gut, respiratory tract, genital track, etc) both IgA1 and IgA2 are present, synthesized by local B cells. In the blood, however, IgA1 predominates, and its origin is B cells in the bone marrow, lymph nodes, and spleen (Donadio and Grande, N Engl J Med, Vol. 347, No. 10: 738-748).

The main difference between the IgA1 and IgA2 subclasses is a 13-amino acid deletion in the IgA2 hinge region. This segment in IgA1 contains several Ser and Thr amino acid residues that are O-glycosylated, but the deletion of this region in IgA2 results in IgA2 having no O-linked oligosaccharides (FIG. 1). IgA1 also has two N-linked carbohydrates in the CH2 (Asn263) and in CH3 (Asn459) domains. All IgA2 allotypes have two additional N-linked sites, in CH1 (Asn166) and in $CH_2$ (Asn337). The IgA2m(2) and the IgA2 (n) allotypes have a fifth N-linked site in CH1 (As211). N-linked glycans are complex structures attached to specific asparagine residues and are common on circulating proteins. In contrast, O-glycans as in the IgA1 hinge consist of simple sugar chains connected to serine or threonine residues, and while abundant on all-surface proteins, they are uncommon on circulating proteins. In IgA1 each O-glycan has a core N-acetyl galactosamine (GalNAc) unit in O-linkage with serine or threonine, and the chain may be extended by the sequential addition of galactose (Gal) in β1,3 linkage with GalNAc, and with one or two sialic units in α2,3 linkage with Gal or α2,6 linkage with GalNAc (Allen et al., J Am Soc Nephrol 10: 1763-1771, 1999; Taj et al., J. Bio. Chem. 1998, 273:4:2260-72). Thus, each O-glycan may consist of one of four different forms, and are identical to those displayed by membrane-bound proteins such as mucins.

The sequence and structure of IgA1 are known in the art and may be used to design polypeptide molecules which may specifically bind to IgA1 or a fragment thereof. For example, the sequence of the heavy and light chain variable domains are provided in GenBank Accession entries AAF03880 (IgA1 kappa light chain; SEQ ID NO: 6), P01708 (IgA1 lambda light chain; SEQ ID NO: 7), and P01773 (IgA1 heavy chain; SEQ ID NO: 8). Of particular interest as a binding target is the constant region of IgA1, and specifically the hinge region which, as noted above, has abnormal glycosylation patterns in individuals with IgA1 deposition disease. The sequence of the IgA1 C-region is shown below (GenBank accession number A1HU; SEQ ID NO: 9). The hinge region is underlined (SEQ ID NO: 10).

N-linked glycan molecules or chains. Without being bound to any particular theory, it is believed that abnormal IgA1 glycosylation patterns observed in individuals with IgA1 deposition disease may lead to aberrant IgA1 deposition, and thus binding IgA1 with an IgA1 binding protein comprising the proper O- or N-linked glycan molecules can decrease the amount of circulating abnormally glycosylated IgA1 and be useful to treat IgA1 deposition disease.

IgA1 binding proteins useful in the invention include polypeptides which bind to IgA1 to the substantial exclusion of any other immunoglobulin molecule. Preferably, the IgA1 binding protein specifically binds to IgA1 (or a fragment thereof), wherein specific binding means that an IgA1 binding protein will bind IgA1 (or a fragment thereof) with at least 2-fold greater affinity, and preferably at least 10-fold, 20-fold, 50-fold, 100-fold or higher affinity than it binds a non-specific molecule (i.e., a non-IgA1 molecule). Alternatively, "specifically binds" as used herein refers to the binding of two protein molecules to each other with a dissociation constant ($K_d$) of 1 μM or lower. For example, the affinity or $K_d$ for a

```
  1   ASPTSPKVFP  LSLCSTQPDG  NVVIACLVQG  FFPQEPLSVT  WSESGQGVTA  RNFPPSQDAS
 61   GDLYTTSSQL  TLPATQCLAG  KSVTCHVKHY  TNPSQDVTVP  CPVPSTPPTP  SPSTPPTPSP
121   SCCHPRLSLH  RPALEDLLLG  SEANLTCTLT  GLRDASGVTF  TWTPSSGKSA  VQGPPERDLC
181   GCYSVSSVLP  GCAEPWNHGK  TFTCTAAYPE  SKTPLTATLS  KSGNTFRPEV  HLLPPPSEEL
241   ALNELVTLTC  LARGFSPKDV  LVRWLQGSQE  LPREKYLTWA  SRQEPSQGTT  TFAVTSILRV
301   AAEDWKKGDT  FSCMVGHEAL  PLAFTQKTID  RLAGKPTHVN  VSVVMAEVDG  TCY
```

Figure 2:
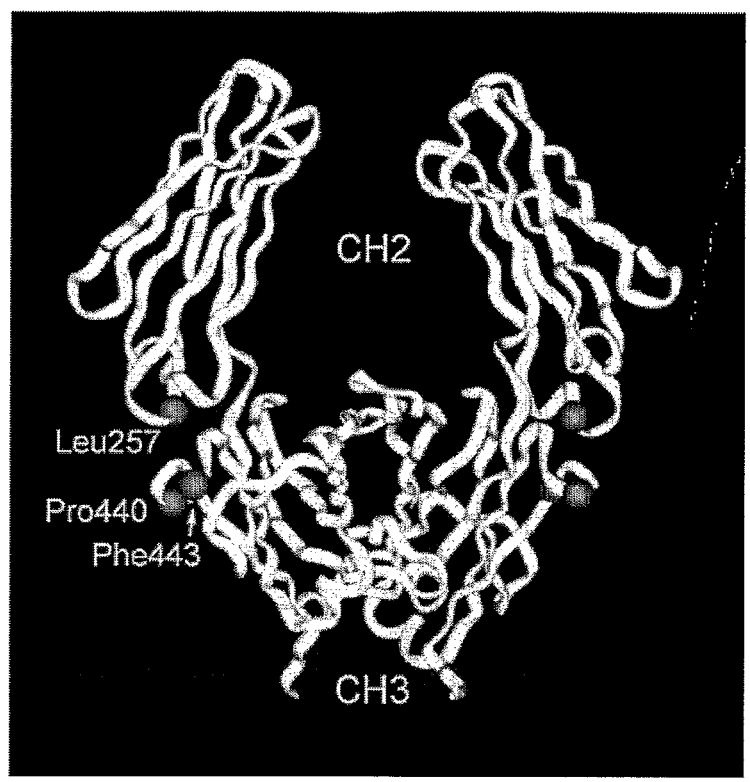
FIG. 2 shows a molecular model of the human IgA1 Fc region.

In one embodiment of the invention, the interface between the CH2 and CH3 domains of IgA1 are of particular interest as a target for binding by an IgA1 binding protein. It will be understood by one of skill in the art that the interface region between CH2 and CH3 is determined by the secondary and tertiary structure of IgA1. Accordingly, molecular modeling of IgA1 will provide sufficient guidance to one of skill in the art to identify the interface between CH2 and CH3. A molecular model of IgA1 is known in the art and taught by Boehm et al. (1999 J. Mol. Biol. 286:1421-47). The CH2 and CH3 interface structure is available through the Rutgers University Protein Data Bank accession number 1iga, and is further shown in FIG. 2.

It is well known in the art that IgA1 monomers can form homodimers with other IgA1 monomers, wherein the IgA1 molecules are linked via a joining (J) chain (Johansen et al., 1999, Eur. J. Immunol. 29:1701) which is produced concomitantly with IgA1 from plasma cells. The sequence of the J chain, although not part of IgA1 may also serve as a useful target for O- or N-linked IgA1 binding proteins. The sequence of the IgA1 J-chain is known in the art (GenBank Accession no. NP_653247) and comprises the sequence:

specific binding interaction can be about 1 μM, or lower, about 500 nM or lower, and about 300 nM or lower. Preferably the $K_d$ for a specific binding interaction is about 300 nM or lower. Specific binding between two molecules (e.g., protein molecules) can be measured using methods known in the art. For example, specific binding may be determined as measured by surface plasmon resonance analysis using, for example, a BIAcore™ surface plasmon resonance system and BIAcore™ kinetic evaluation software (e.g., version 2.1). Alternatively, the binding affinity of an IgA1 binding protein to IgA1 and the off-rate of such an interaction can be determined by competitive binding assays. One example of a competitive binding assay is a radioimmunoassay comprising the incubation of labeled IgA1 (e.g., $^3$H or $^{125}$I) with the IgA1 binding protein of interest in the presence of increasing amounts of unlabeled IgA1, and the detection of the IgA1 binding protein of interest bound to the labeled IgA1. The affinity of the IgA1 binding protein of interest for IgA1 and the binding off-rates can be determined from the data by scatchard plot analysis. Competition with a second IgA1 binding protein can also be determined using radioimmunoassays. In this case, the antigen is incubated with antibody

```
                                                                (SEQ ID NO: 11)
  1   MKNHLLFWGV  LAVFIKAVHV  KAQEDERIVL  VDNKCKCARI  TSRIIRSSED  PNEDIVERNI
 61   RIIVPLNNRE  NISDPTSPLR  TRFVYHLSDL  CKKCDPTEVE  LDNQIVTATQ  SNICDEDSAT
121   ETCYTYDRNK  CYTAVVPLVY  GGETKMVETA  LTPDACYPD
```

IgA1 Binding Proteins

The present invention utilizes proteins which specifically bind IgA1 and which have been modified to comprise O- or of interest conjugated to a labeled compound (e.g., $^3$H or $^{125}$I in the presence of increasing amounts of an unlabeled second antibody. Other methods of determining binding of an IgA1 binding protein of the invention to IgA1 will be readily apparent to one of skill in the art, and include, but are not limited to FRET assays, column elution assays, biosensor assays, Western blotting and the like.

IgA1 binding proteins of the invention include, but are not limited to, antibody polypeptides specific for IgA1: S. pyogenes Sir22 polypeptide, S. aureus protein A modified Z-domain, S. aureus affibody, CD89, Fcα/μR, polymeric Ig receptor, transferrin receptor, Peyer's patch M cell IgA receptor, or a synthetic polypeptide which specifically binds IgA1. Since the amino acid sequence and three dimensional structure of IgA1 is known, IgA1 binding polypeptides of the invention may be selected and/or designed to bind to any portion of the IgA1 molecule or fragment thereof.

Antibody Polypeptides

In one embodiment of the invention, an IgA1 binding protein is an antibody polypeptide which specifically binds to IgA1. An antibody polypeptide, as used herein, refers to an immunoglobulin molecule, or fragment thereof, that is capable of binding IgA1. The term antibody polypeptide preferably does not include whole antibodies, e.g., of any isotype (IgG, IgA, IgM, IgE, etc), but instead refers to fragments thereof which are specifically reactive with IgA1 protein. Antibodies can be fragmented using conventional techniques. Thus, antibody polypeptides useful in the invention include segments of proteolytically-cleaved or recombinantly-prepared portions of an antibody molecule that are capable of selectively reacting with a certain protein. Non limiting examples of such proteolytic and/or recombinant fragments include Fc, Fab, F(ab')2, Fab', Fv, dAbs and single chain antibodies (scFv) containing a $V_L$ and $V_H$ domain joined by a peptide linker. The scFv's may be covalently or non-covalently linked to form antibody polypeptides having two or more binding sites. Thus, antibody polypeptides include polyclonal, monoclonal, or other purified preparations of antibody polypeptides and recombinant antibody polypeptides. In a preferred embodiment, an antibody polypeptide which binds to IgA1 is a Fab.

Antibody polypeptides of the invention which specifically bind IgA1 may be either naturally occurring or may be generated by methods which are well known in the art. IgA1 or fragments thereof may be used to induce specific antibodies provided a fragment has an amino acid sequence comprising at least five amino acids. For the production of antibodies, various hosts including goats, rabbits, rats, mice, etc., may be immunized by injection with IgA1 (or any portion, fragment, or oligonucleotide thereof which retains immunogenic properties). Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

To generate polyclonal antibodies, IgA1 may be conjugated to a conventional carrier in order to increase its immunogenicity, and an antiserum to the IgA1-carrier conjugate raised. Coupling of a peptide to a carrier protein and immunizations may be performed as described in Dymecki et al., 1992, *J. Biol. Chem.*, 267:4815. The serum can be titered against IgA1 antigen by ELISA (below) or alternatively by dot or spot blotting (Boersma & Van Leeuwen, 1994, *J. Neurosci. Methods*, 51:317). A useful serum will react strongly with the IgA1 by ELISA, for example, following the procedures of Green et al., 1982, *Cell*, 28:477.

Techniques for preparing monoclonal antibodies are well known, and are described, for example, by Arnheiter et al., 1981, *Nature*, 294:278. Monoclonal antibodies are typically obtained from hybridoma tissue cultures or from ascites fluid obtained from animals into which the hybridoma tissue was introduced. Monoclonal antibody-producing hybridomas (or polyclonal sera) can be screened for antibody binding to IgA1 according to methods known in the art. For example, the nucleic acid sequence encoding heavy and light chains of an antibody known to bind IgA1 can be manipulated to generate a number of different antibody polypeptides that are specific for IgA1 binding. Thus, given the sequences encoding the heavy and light chain polypeptides that constitute an antibody and standard molecular cloning methodologies, one can generate IgA1-binding polypeptide constructs such as Fab fragments, scFv, dAbs, or even bispecific antibodies (i.e., antibodies that comprise two different antigen-binding moieties and can therefore bind two separate antigens, preferably simultaneously) that are specific for IgA1.

Thus, one means of generating antibody polypeptides specific for IgA1 is to amplify and express the $V_H$ and $V_L$ regions of the heavy chain and light chain gene sequences isolated, for example, from a hybridoma (e.g., a mouse hybridoma) that expresses anti-IgA1 monoclonal antibody. The boundaries of the $V_H$ and $V_L$ domains of heavy and light chain genes are used to design PCR primers that amplify the V domain from a heavy or light chain coding sequence encoding an antibody known to bind IgA1. The amplified V domains are inserted into a suitable expression vector, e.g., pHEN-1 (Hoogenboom et al., 1991, Nucleic Acids Res. 19: 4133-4137) and expressed, e.g., as a fusion of the $V_H$ and $V_L$ in an scFv or other suitable format. The resulting polypeptide is then screened for high affinity binding to IgA1. For all aspects of the present invention, screening for binding is performed as known in the art or as described herein above.

Alternatively, library screening methods can be used to identify IgA1-specific antibody polypeptides. Phage display technology (see, e.g., Smith, 1985, Science 228: 1315; Scott & Smith, 1990, Science 249: 386; McCafferty et al., 1990, Nature 348: 552) provides an approach for the selection of antibody polypeptides which bind a desired target from among large, diverse repertoires of antibody polypeptides. These phage-antibody libraries can be grouped into two categories: natural libraries which use rearranged V genes harvested from human B cells (Marks et al., 1991, J. Mol. Biol., 222: 581; Vaughan et al., 1996, Nature Biotech., 14: 309) or synthetic libraries whereby germline V gene segments or other antibody polypeptide coding sequences are 'rearranged' in vitro (Hoogenboom & Winter, 1992, J. Mol. Biol., 227: 381; Nissim et al., 1994, EMBO J., 13: 692; Griffiths et al., 1994, EMBO J., 13: 3245; De Kruif et al., 1995, J. Mol. Biol., 248: 97) or where synthetic CDRs are incorporated into a single rearranged V gene (Barbas et al., 1992. Proc. Natl. Acad. Sci. USA, 89: 4457). Methods involving genetic display packages (e.g., phage display, polysome display) are well-suited for the selection of IgA1-specific antibody constructs because they generally express only monovalent fragments, rather than whole, divalent antibodies, on the display packages. Methods for the preparation of phage display libraries displaying various antibody fragments are described in the preceding references. Such methods are also described, for example, in U.S. Pat. No. 6,696,245, which is incorporated herein by reference. The methods described in the '245 patent generally involve the randomization of selected regions of immunoglobulin gene coding regions, in particular $V_H$ and $V_L$ coding regions, while leaving other regions non-randomized (see below). The '245 patent also describes the generation of scFv constructs comprising individually randomized $V_H$ and $V_L$ domains.

The $V_H$ gene is produced by the recombination of three gene segments, $V_H$, D and $J_H$. In humans, there are approximately 51 functional $V_H$ segments (Cook and Tomlinson (1995) Immunol Today 16: 237), 25 functional D segments (Corbett et al. (1997) J. Mol. Biol. 268: 69) and 6 functional $J_H$ segments (Ravetch et al. (1981) Cell 27: 583), depending on the haplotype. The $V_H$ segment encodes the region of the polypeptide chain which forms the first and second antigen binding loops of the $V_H$ domain (H1 and H2), while the $V_H$, D and $J_H$ segments combine to form the third antigen binding loop of the $V_H$ domain (H3).

The $V_L$ gene is produced by the recombination of only two gene segments, $V_L$ and $J_L$. In humans, there are approximately 40 functional $V_\kappa$ segments (Schäble and Zachau (1993) Biol. Chem. Hoppe-Seyler 374: 1001), 31 functional $V_\lambda$ segments (Williams et al. (1996) J. Mol. Biol. 264: 220; Kawasaki et al. (1997) Genome Res. 7: 250), 5 functional $J_\kappa$ segments (Hieter et al. (1982) J. Biol. Chem. 257: 1516) and 4 functional $J_\lambda$ segments (Vasicek and Leder (1990) J. Exp. Med. 172: 609), depending on the haplotype. The VL segment encodes the region of the polypeptide chain which forms the first and second antigen binding loops of the VL domain (L1 and L2), while the VL and JL segments combine to form the third antigen binding loop of the VL domain (L3). Accordingly, antibodies selected from this primary repertoire are believed to be sufficiently diverse to bind almost all antigens with at least moderate affinity. High affinity antibodies are produced in vivo by "affinity maturation" of the rearranged genes, in which point mutations are generated and selected by the immune system on the basis of improved binding. Additional methods for the production of antibody polypeptides against IgA1 using phage display are described in Kay et al., Phage Display of Peptides and Proteins: A Laboratory Manual, (Academic Press, Inc.; San Diego 1996) and U.S. Pat. No. 5,223,409 (Ladner et al.), both of which are incorporated herein by reference in their entirety. Antibody libraries which are of particular interest to screen for IgA1 binding include those produced by Cambridge Antibody Technology (Cambridge, UK). To isolate antibodies to a target molecule the entire library is incubated with it, and antibodies that bind are selected for expansion. This allows for more rapid identification and isolation of antibodies and avoids the need for immunization of animals. Phage display has an additional advantage, allowing production only of Fab fragments that specifically bind to IgA. Also these proteins can be expressed with a Ser/Thr rich, or Asn rich motif at the C-terminus of the H or L chain, providing sites for conjugative addition of O-linked trisaccharides.

Many published examples of how to make a therapeutic mAb are available. (Mitchell et al., Cancer Control March/April 2002, Vol. 9, No. 2, 152-166; Gorman and Clark "Humanisation of Monoclonal Antibodies for Therapy" Cambridge University, Department of Pathology, Immunology Division, Tennis Court Road, Cambridge Cβ2 1QP; "Antibodies as Medicines" 2000 by Biotech Analytics). With respect to IgA1 as antigen, there are 3 regions which are preferred to use as antigen against which to raise antibody polypeptides: a) the IgA1 hinge region. Since the hinge region of IgA1 is unique between IgA1 and IgA2, antibody to it should readily differentiate it from the hinge of IgA2, and it is IgA1 that is involved in a number of IgA deposition diseases targeted for treatment. There are two specific binding sites in the hinge region of IgA1 useful for raising an anti-IgA1 antibody polypeptide: i) the primary amino acid sequence of the hinge region; and ii) the exposed GalNAc residues in the O-linked glycans that are characteristic of these abnormally glycosylated IgA proteins. The binding to GalNAc residues may be preferable, because in IgA nephropathy, it is known that these patients have high-levels of IgG antibodies that are specific for (directed against) GalNAc residues exposed on the IgA hinge region. This promotes formation of circulating immune complexes (CICs). Thus, the binding of an antibody polypeptide raised in an animal to the exposed GalNAc residues could block the formation of CICs. b) the CD89 binding site of IgA. An Fab produced to this antigen will have the effect of preventing CD89 binding, and thus preventing activation of inflammation. c) The constant region of the IgA heavy chain within the Fab domain of the protein, the CH1 domain. Antibody to this site will be unlikely to block access of IgA proteases for hinge region cleavage.

In a preferred embodiment, the antibody polypeptide is designed to bind the hinge region of IgA1, the sequence of which is shown in SEQ ID NO: 10. More preferably, the antibody polypeptide is designed to recognize and specifically bind the hinge region having the amino acid sequence TPPTPSPSTPPTPSPS (SEQ ID NO: 12). In another embodiment, an antibody polypeptide is produced to bind to the CD89 binding site, which is the $CH_2$—$CH_3$ interface. The CD89 binding site may be determined by one of skill in the art using the three dimensional structure and molecular coordinates which are known in the art and taught by Boehm et al. (1999 J. Mol. Biol. 286:1421-47). The CH2 and CH3 interface structure is available through the Rutgers University Protein Data Bank accession number 1iga, and is further shown in FIG. 2. In yet another embodiment, an antibody polypeptide of the invention may be designed to bind to the CH1 region of the heavy chain constant domain. The sequence of the CH1 domain is known in the art and is shown in SEQ ID NO: 9 as the sequence antecedent to the hinge region.

In one embodiment the antibody polypeptides of the invention are human antibody polypeptides. In a further embodiment, the antibody polypeptides have been humanized. A human antibody polypeptide refers to an antibody polypeptide which specifically binds to anti-IgA1 (or a portion thereof as described above), and which has a sequence derived from a human immunoglobulin. A sequence is derived from a human immunoglobulin coding sequence when the sequence is either: a) isolated from a human individual or from cells or a cell line from a human individual; b) isolated from a library of cloned human antibody gene sequences (or a library of human antibody V domain sequences); c) when a cloned human antibody gene sequence (or a cloned human V region sequence (including, e.g., a germline V gene segment)) was used to generate one or more diversified sequences that were then selected for binding to a desired target antigen; or d) isolated from a transgenic animal (e.g., rodent) which has been modified to express human antibody genes, such that the transgenic animal will generate human antibodies against an introduced antigen. Similarly, a humanized antibody polypeptide refers to an antibody polypeptide, as defined herein, in which the light and/or heavy chain V region complementarity determining regions (CDRs) are of animal origin (e.g., rodent), but which has been modified to replace constant region and/or variable region framework sequences with sequences of human origin, while retaining the original antigen specificity (e.g., IgA1). Different degrees of humanization can be achieved, however, ranging from chimeric antibodies with a combination of human constant regions with rodent variable regions to fully reshaped antibodies where the variable regions are also humanized. Methods for the humanization of antibody polypeptides are reviewed in Gorman and Clark (Semin Immunol. 1990 November; 2(6):457-66), and taught further in, for example, Oi et al., (1983) Proc. Natl. Acad. Sci. USA 80:825-829; Neuberger et al., Nature 314, 268-271; Sharon et al. (1984) Nature 309:364-367; Jones et al., Nature 321, 522-5; Riechmaim et al., (1988) Nature 332, 323-327; and Verhoeyen et al., (1988) Science 239, 1534-1536.

SIR22

In another embodiment of the invention, an IgA1 binding protein useful in the invention is the Sir22 protein isolated from *Streptococcus pyogenes*. Sir22 is known to bind to IgA1, and may be modified according to the methods described herein to include a non-naturally occurring O- or N-linked glycan. Sir22 is known in the art and described in, for example, Stenberg et al. (1994, J. Biol. Chem. 269:13458; coding sequence is taught in GenBank Accession No. SPMRP22). In a preferred embodiment, an IgA1 binding protein useful in the invention includes a portion of Sir22 comprising the amino acid sequence is shown in SEQ ID NO: 2. This domain of Sir22 is known to bind only to serum and secretory IgA1, and not to other classes of Ig, and is known to bind IgA in both free and immobilized forms. The Sir22 peptide binds to IgA1 at the CH2-CH3 interdomain region, which is also the site bound by human CD89 (which, as described further, is an IgA1 receptor). Without being bound to a single theory, it is believed that blocking this site will reduce interaction of the IgA1 with CD89, thus preventing cytokine release from myeloid cells at sites of IgA1 deposition. In one embodiment, the IgA1 binding protein comprises amino acid residues 11-29 of SEQ ID NO: 2. This sequence is known to be the core IgA1 binding motif, although addition of at least ten extra residues on either side of this region is preferred for reinforcement of IgA1 binding. Although described in further detail below, in one embodiment, the sequence of SEQ ID NO: 2 is modified by the N-terminal addition of six additional amino acids comprising Ser/Thr or Asn for the addition of O- or N-linked glycans, respectively. In one embodiment, the sequence of SEQ ID NO: 2 is modified by the addition of the sequence TPPTPS (SEQ ID NO: 13) to the N-terminal end to yield a 55 residue amino acid sequence.

The sequence of the entire streptococcal protein Sir 22 is published in Stenberg et al., 1994, Molecular Characterization of Protein Sir, a Streptococcal Cell Surface Protein That Binds Both immunoglobulin A and Immunoglobulin G, The Journal of Biological Chemistry Vol. 269, No. 18, 13458-13464. The nucleic acid and amino acid sequence of Sir22 may be found at GenBank Accession No. X75750 and is shown below (SEQ ID NO: 1).

```
                                                     SEQ ID NO: 1
            5         10         15         20         25         30
  1 M A R K D T N K Q Y S L R K L K T G T A S V A V A V A V L G

31 A G F A N Q T T V K A E S S N N A E S S N I S Q E S K L I N

61 T L T D E N E K L R E E L Q Q Y Y A L S D A K E E E P R Y K

91 A L R G E N Q D L R E K E R K Y Q D K I K K L E E K E K N L

121 E K K S E D V E R H Y L K K L D Q E H K E Q Q E R Q K N L E

151 E L E R Q S Q R E I D K R Y Q E Q L Q K Q Q Q L E T E K Q I

181 S E A S R K S L S R D L E A S R A A K K K V E A D L A A L N

211 A E H Q K L K E E K Q I S D A S R Q G L S R D L E A S R E A

241 K K K V E A D L A E A N S K L Q A L E K L N K E L E E G K K

271 L S E K E K A E L Q A R L E A E A K A L K E Q L A K Q A E E

301 L A K L G N Q T P N A K V A P Q A N R S R S A M T Q Q K R

331 T L P S T G E A A N P F F T A A A A T V M V S A G M L A L K

361 R K E E N
```

In the sequence, residues 1-41 comprise the signal sequence. Mature protein starts from residue 42. The underlined sequence is the actual 49-residue IgA binding peptide: Y Y A L S D A K E E E P R Y K A L R G E N Q D L R E K E R K Y Q D K I K K L E E K E K N L E K K S (SEQ ID NO: 2; see Johnsson, et. al. J Biol Chem, Vol. 274, Issue 21, 14521-14524, May 21, 1999). The nucleic acid sequence encoding Sir22 is shown below (SEQ ID NO: 3)

```
   1  AAGCTTCAGG AGCTCAAAAA CCAGATACTA AACCTGGCAA TAAAGAGGTT CCAACA

```
  1  MEQRITLKEA WDQRNGFIQS LKDDPSQSAN VLGEAQKLND SQAPKADAQQ NNFNKDQQSA

61  FYEILNMPNL NEAQRNGFIQ SLKDDPSQST NVLGEAKKLN ESQAPKADNN FNKEQQNAFY

121  EILNMPNLNE EQRNGFIQSL KDDPSQSANL LSEAKKLNES QAPKADNKFN KEQQNAFYEI

181  LHLPNLNEEQ RNGFIQSLKD DPSQSANLLA EAKKLNDAQA PKADNKFNKE QQNAFYEILH

241  LPNLTEEQRN GFIQSLKDDP GNSRGSVDLQ ITN
```

In Protein A, one can find five Ig binding domains. One of these is the so-called B domain, indicated as the underlined peptide stretch above. Using the B domain as a platform, other laboratories created a non-native Z domain, and expressed this as a recombinant protein. Since B and Z domains are IgG binding, variants of the Z-domain were generated to identify sequences which would bind to IgA1. Modified Z-domains were developed by phage display technology, in which several amino acid residues in the Z domain were changed to turn the whole molecule from being an IgG binding peptide to an IgA binding peptide (Rönnmark et al., Eur. J. Biochem. 269, 2647-2655 (2002)). The original IgG binding affinity was completely lost, with this modification.

In a preferred embodiment, the IgA1 binding protein is a 58 amino acid fragment of a protein A modified Z-domain, comprising the sequence of SEQ ID NO: 5: VDNKFNKETIQA SQEIRLLPNLNGRQKLAFIHSLLD-DPSQSANLLAEAKKLNDAQAPK. Preferably, a modified Z-domain protein sequence of use in the invention as an IgA1 binding protein comprises the sequence of SEQ ID NO: 5. Other modified Z-domain sequences which have been shown to bind to IgA1 may also be used according to the invention, and include, but are not limited to those taught by Ronnmark et al, supra.

IgA1 Receptors

Human beings have three major IgA receptors: FcαR1 (CD89), asialoglycoprotein receptor (ASGPR), and polymeric Ig receptors (pIgR). Given their ability to bind to IgA1, each of these receptors may be used according to the invention as an IgA1 binding protein for the removal of IgA1 in the circulation, and/or the treatment of IgA1 deposition disease.

Human FcαR1 (CD89)

Interaction of IgA with the human FcαR (CD89) may be important in inflammatory changes of the kidney in IgA nephropathy. The CD89 protein is a membrane glycoprotein that contains two extracellular Ig-like domains (206 aa), a membrane-spanning region (19 aa), and a cytoplasmic tail of 31 aa. At the transmembrane region, there is a positively charged Arg that is necessary for association of CD89 with the FcR γ-chain. Like other Fc receptors lacking an intracellular signaling motif, FcαR's signaling into the cell is initiated via its association with FcR γ-chain. The FcR γ-chain is a homodimer-signaling unit with a size of 10 kDa. Binding to CD89 leads to phosphorylation of the intracellular, tyrosine-based ITAM motifs on the γ-chain, activating the signaling pathways downstream into the cell. FcαR1 binds both the monomeric and dimeric forms of IgA1 and IgA2 (Herr et al., 2003, Nature 423:624; Herr et al., 2003, J. Mol. Biol. 327: 645). Transfection studies in leukocytes showed that the FcαR1 does not bind IgG. FcaR1 is expressed by neutrophils, monocytes, macrophages, and eosinophils. It was proposed that FcaR1 plays a role in the removal of IgA-antigen complexes from the circulation (Taj et al., J. Bio. Chem. 1998, 273:4:2260-72; Leung et al., J Am Soc Nephrol 11:241-249, 2000; and Westerhuis Pathogenetic *Aspects of IgA-Nephropathy* 2001, Chapter 1, Section IV: IgA receptors and IgAN, Printed by PrintPartners, Ipskamp, Enschede). It is worth noting that all the myeloid cells mentioned above that express CD89 show antibody dependent cell-mediated cytotoxicity (ADCC), adding to potential for tissue injury. Furthermore, the crosslinking of CD89 with IgA will trigger these myeloid cells to release cytokines, including TNFα, IL-1α, and IL-6. These local events can promote IgA-induced renal damage.

CD89 may be modified as described below by expressing the soluble portion with the addition of one or more O- or N-linked glycans to either naturally occurring or artificially introduced serine/threonine, or asparagine residues, respectively, and used to decrease the amount of IgA1 in an individual or to treat a disease in an individual characterized by IgA1 deposition.

Polymeric Ig Receptor

The polymeric Ig receptor (pIgR) is an integral membrane component localized on the basolateral surface of secretory epithelial cells (Mostov et al., Curr Opin Cell Biol. 2000 August; 12 (4):483-90; Mostov, (1994) Annual Review of Immunology, Vol. 12: 63-84). It mediates the transepithelial transport of polymeric Ig, mainly dimeric IgA and pentameric IgM. pIgR is on most human secretory epithelia, including intestine, bronchus, salivary glands, renal tubule, and uterus, and it binds to J chains on polymeric immunoglobulins. Binding of IgA results in the protein being transferred from the lamina propria of the mucosa through the epithelial cell to the gut (or other IgA secretory sites) to reach the cell free fluids bathing the mucus membranes. Secretory IgA (sIgA) is responsible for neutralization of microbes and toxins and prevents unwanted antigens to pass the mucosal barrier (Taj et al., J. Bio. Chem. 1998, 273:4:2260-72; Joseph et al., J Am Soc Nephrol 11:241-249, 2000). Since pIgR transports IgA that is produced from local mucosal B-cells or plasma cells, it is not a route for serum IgA clearance. Further, there is no evidence that sIgA is involved in IgAN or other IgA deposition diseases. Accordingly, one of skill in the art may use all or a portion of the polymeric Ig receptor (secretory component (SC) portion of pIgR) as an IgA1 binding protein in the present invention.

Asialoglycoprotein Receptor (ASGPR)

The asialoglycoprotein receptor (ASGPR) is a C-type lectin that recognizes galactose and N-acetylgalactosamine residues of desialylated glycoproteins, and it mediates endocytosis of serum glycoproteins (Leung et al., J Am Soc Nephrol 11:241-249, 2000; Westerhuis, Pathogenetic Aspects of IgA-Nephropathy 2001, Chapter 1, Section IV: IgA receptors and IgAN, Printed by PrintPartners, Ipskamp, Enschede; and Ishibashi et al., J. Biol. Chem., Vol. 269, Issue 45, 27803-27806, 11, 1994). ASGPR is predominantly expressed on the sinusoidal surface of the hepatocytes. ASGPR is abundant, with approximately 500,000 receptors/hepatocyte. The human ASGPR is an integral transmembrane glycoprotein composed of two units, HL1 and HL2 (HL stands for Hepatic Lectin). The assembly of two homologous subunits, HL-1 and HL-2 as a heterooligomer is required to yield functional and high affinity receptors on the cell surface. In 1974 Ashwell and Morell discovered the ASGPR by noting that the liver rapidly removed serum glycoproteins having terminal galactose residues. The proposed physiological and pathophysiological functions of this receptor include the removal of desialylated serum glycoproteins and apoptotic cells, clearance of chylomicron remnants, and as a homing receptor for lymphatic and metastatic cells. Among the desialylated serum glycoproteins removed by this receptor are IgA1 and IgA2.

In plasma proteins, however, terminal sialic acid residues mask the penultimate galactose residues of oligosaccharide side chains. With time the sialic acids are lost from these proteins, thus exposing the underlying galactose residues, and this marks the proteins for uptake by the ASGPR. Those proteins are then eliminated by endocytosis. This is a major mechanism of IgA1 clearance in human beings, and cannot take place if IgA1 is underglycoslated, and specifically where IgA1 does not display terminal galactose residues. Also, when ASGPR function is severely impaired by liver disease, serum IgA1 levels may rise, and secondary IgA nephropathy can occur (Pouria and Feehally, Nephrol Dial Transplant (1999) 14: 2279-2282). Indeed, IgA nephropathy associated with liver disease (hepatic IgAN) is the commonest form of secondary IgAN.

Other IgA1 Receptors

In addition to those IgA1 binding proteins described above, one of skill in the art will appreciate that any protein which is known to bind IgA, or to function as a receptor for IgA1 may be useful in the invention as an IgA1 binding protein which may be modified by the addition of O- or N-linked glycans. Other useful IgA1 binding proteins include, but are not limited to, the transferrin receptor (CD71) expressed on masangial cells (Haddad et al., J Am Soc Nephrol 14: 327-337, 2003), the Fcα/μR receptor which is expressed on both hematopoietic and non-hematopoietic tissues (Monteiro and van de Winkel, (2003) Annual Review of Immunology Vol. 21: 177-204; Sakamoto et al, (2001) European Journal of Immunology, Vol 31, Issue 5, Pages 1310-1316; Shibuya et al., (2000) Nature Immunology 1, 441-446, and an IgA receptor on Peyer's patch M cells that selectively binds and endocytoses secretory IgA antibodies (Mantis et al., J. Immunol, 2002, 169: 1844-1851). The amino acid sequence of the transferrin receptor is known in the art and may be found, for example, at GenBank Accession No. NP_003225. Likewise the amino acid sequence of the Fcα/μR IgA receptor is known and may be found at AY063125. Accordingly, one of skill in the art will readily appreciate that either of these receptor sequences may be modified by the addition of one or more O- or N-linked glycans to either naturally occurring or artificially introduced serine/threonine, or asparagine residues, respectively, and subsequently used to decrease the amount of IgA1 in an individual or to treat a disease in an individual characterized by IgA1 deposition.

Homologs/Variants

In addition to the specific sequences of the IgA1 binding proteins described above, and herein, the invention contemplates that variants of these sequences may be used according to the invention but which still substantially retain the ability to specifically bind IgA1.

Homology between two or more IgA1 binding proteins refers to the degree with which two nucleotide or amino acid sequences structurally resemble each other. Sequence similarity is a measure of the degree to which amino acid sequences share similar amino acid residues at corresponding positions in an alignment of the sequences. Amino acids are similar to each other where their side chains are similar. Specifically, similarity or homology encompasses amino acids that are conservative substitutes for each other. A conservative substitution is any substitution that has a positive score in the blosum62 substitution matrix (Hentikoff and Hentikoff, 1992, Proc. Natl. Acad. Sci. USA 89: 10915-10919). For example, by the statement "sequence A is n % similar to sequence B" is meant that n % of the positions of an optimal global alignment between sequences A and B consists of identical amino acids or conservative substitutions (wherein, for example, sequence A is an IgA1 binding protein as described above, and sequence B is a variant thereof). Optimal global alignments can be performed using the following parameters in the Needleman-Wunsch alignment algorithm:

For polypeptides:
Substitution matrix: blosum62.
Gap scoring function: -A-B*LG, where A=11 (the gap penalty), B=1 (the gap length penalty) and LG is the length of the gap.

Although many of the IgA1 binding proteins described above are presented by amino acid sequence, it will be understood by one of skill in the art that the nucleic acid sequence which encodes the above-referenced amino acid sequences would also encompass homologous sequences or variants. Accordingly, global alignments between two nucleic acid sequences can be performed using the following parameters in the Needleman-Wunsch alignment algorithm:

Substitution matrix: 10 for matches, 0 for mismatches.
Gap scoring function: -A-B*LG where A=50 (the gap penalty), B=3 (the gap length penalty) and LG is the length of the gap.

Typical conservative substitutions are among Met, Val, Leu and Ile; among Ser and Thr; among the residues Asp, Glu and Asn; among the residues Gln, Lys and Arg; or aromatic residues Phe and Tyr.

As used herein, two sequences are "homologous" or "similar" to each or a "variant" of each other where they have at least 85% sequence similarity to each other, including, e.g., 90%, 95%, 97%, 99% or even 100% sequence similarity, when aligned using either the Needleman-Wunsch algorithm or the "BLAST 2 sequences" algorithm described by Tatusova & Madden, 1999, FEMS Microbiol Lett. 174:247-250. Where amino acid sequences are aligned using the "BLAST 2 sequences algorithm," the Blosum 62 matrix is the default matrix. In addition a particular peptide sequence is a variant or homolog of an IgA1 binding protein as described above, if the above sequence identity criteria are met and the variant or homolog binds IgA1 with a specificity which is not reduced by more than 10% relative to the binding specificity of an IgA1 binding protein sequence described herein. It is also contemplated that a variant or homolog of an IgA1 binding protein described herein may have a greater IgA1 binding affinity.

O- or N-Linked Glycan

According to the invention, peptides which bind IgA1 are modified to include either or both of O- or N-linked glycan molecules. O-linked glycan molecules or chains will be linked to one or more of serine and/or threonine residues present in the IgA1 binding protein. Likewise, N-linked glycan molecules or chains will be linked to one or more asparagine residues in the IgA1 binding protein.

O-Linked Glycans

In one embodiment an IgA1 binding protein of the invention includes one or more serine or threonine residues which are modified by the addition of an O-linked glycan. The serine or threonine residues may be naturally occurring in the IgA1 binding protein, or they may be artificially introduced into the polypeptide sequence of the IgA1 binding protein. Methods for modifying a polypeptide sequence to include non-naturally occurring residues are known in the art and include random or site directed mutagenesis. See, for example, Ausubel et al., (eds.) CURRENT PROTOCOLS IN MOLECULAR BIOLOGY (Wiley Interscience, 1987); PROTEIN ENGINEERING (Oxender & Fox eds., A. Liss, Inc. 1987). These methods require the availability of a gene encoding an IgA1 binding protein of the invention or a variant thereof, which can then be mutagenized by known methods to include attachment motifs for either or both of O- or N-linked glycans. In addition, linker-scanning and polymerase chain reaction ("PCR") mediated techniques can be used for purposes of mutagenesis. See PCR TECHNOLOGY (Erlich ed., Stockton Press 1989); CURRENT PROTOCOLS IN MOLECULAR BIOLOGY, vols. 1 & 2, loc. cit. In a preferred embodiment, a mixed serine/threonine rich region of between 2 and 20 amino acid residues is added to either or both of the N- and C-terminal end of the IgA1 binding protein. For example, the Ser/Thr rich region may contain between 2 and 20 Ser/Thr residues, between 2 and 15, between 3 and 10, and preferably between 3 and 6 serine and threonine residues. In one embodiment, the Ser/Thr rich region has the sequence TPSPS. The addition of serine and threonine residues provides sites for O-linked glycosylation by chemical or chemoenzymatic synthesis.

O-linked glycans as used herein refer to a polymers comprising a plurality (e.g., two or more) of monosaccharide residues joined to each other by glycosidic linkages, wherein the polymer comprises at least one galactose residue which is linked (directly or indirectly) to the hydroxyl group of an amino acid side chain. The galactose is further linked optionally to a sialic acid (S.A.) molecule. An O-linked glycan of the invention preferably has the following structure:

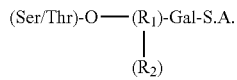

wherein, (Ser/Thr) is one or more non-naturally occurring serine or threonine residues which is either naturally occurring or has been introduced into an IgA1 binding protein and modified by the addition of the O-linked glycan;

wherein S.A. is a sialic acid;

wherein, $R_1$ is H, $(GalNAc)_n$, where n=1, 2, 3, 4, 5, 6, 7, 8, 9, or 10;

and wherein when $R_1$ is $(GalNAc)_n$, $R_2$ is S.A.

As used herein, GalNAc refers to N-acetyl galactosamine. Preferred examples of O-linked glycans which may be used according to the invention include, but are not limited to the following:

---

A. Ser/Thr-O-GalNAc (also referred to as the Tn antigen; Allen et al., 1999, J. Am. Soc. Nephrol. 10: 1763)

B. Ser/Thr-O-GalNAc-Gal (also referred to as the T antigen; Allen et al., supra)

C. Ser/Thr-O-GalNAc-Gal-S.A.

D. Ser/Thr-O-GalNAc-Gal-S.A.
   S.A.

---

One of skill in the art will appreciate, however, that longer or branched forms of the above listed O-linked glycan chains may be used.

Addition of O-linked glycans to serine and/or threonine residues of the IgA1 binding proteins of the instant invention may be accomplished using methods which are well known in the art. For example, methods for the synthesis of glycopeptides, and carbohydrate side chains are described in Dudkin et al., 2004, J. Am. Chem. Soc. 126:9560 and Dudkin et al., 2004, J. Am. Chem. Soc. 126: 736. Alternatively, a number of commercial manufacturers of synthetic glycopeptides may be utilized to produce the O-linked glycan IgA1 binding proteins of the invention. Synthetic glycopeptides may be obtained, for example, from Dextra Laboratories Reading, UK (on the world wide web at dextra-labs.co.uk/default.asp), GlycoFi Inc. (Lebanon, N.H. and on the world wide web at glycofi.com/glycoproteins.htm), Momanta Pharmaceuticals, Inc. (Cambridge, Mass. and on the world wide web at momentapharma.com), and Optimer Pharmaceuticals, Inc (San Diego, Calif. and on the world wide web at optimerpharma.com).

N-Linked Glycans

In one embodiment an IgA1 binding protein of the invention includes one or more asparagine residues which are modified by the addition of an N-linked glycan. The asparagine residues may be naturally occurring in the IgA1 binding protein, or they may be artificially introduced into the polypeptide sequence of the IgA1 binding protein. Preferably, the asparagine residue is artificially introduced into an IgA1 binding protein of the invention. Methods for modifying a polypeptide sequence to include non-naturally occurring residues are known in the art and include random or site directed mutagenesis See, for example, Ausubel et al., (eds.) CURRENT PROTOCOLS IN MOLECULAR BIOLOGY (Wiley Interscience, 1987); PROTEIN ENGINEERING (Oxender & Fox eds., A. Liss, Inc. 1987). These methods require the availability of a gene encoding an IgA1 binding protein of the invention or a variant thereof, which can then be mutagenized by known methods to include attachment motifs for either or both of O- or N-linked glycans. In addition, linker-scanning and polymerase chain reaction ("PCR") mediated techniques can be used for purposes of mutagenesis. See PCR TECHNOLOGY (Erlich ed., Stockton Press 1989); CURRENT PROTOCOLS IN MOLECULAR BIOLOGY, vols. 1 & 2, loc. cit. In a preferred embodiment, an asparagine rich region of between 1 and 20 amino acid residues is added to either or both of the N- and C-terminal ends of the IgA1 binding protein. For example, the asparagine rich region may contain between 1 and 20 Asn residues, between 1 and 10, between 2 and 5, and preferably between 1 and 4 asparagine residues. In one embodiment, the asparagine region has the sequence ANL. The addition of asparagine residues provides sites for N-linked glycosylation by chemical or chemoenzymatic synthesis.

An N-linked glycan refers to a glycan attached to a protein through the side chain (amide) nitrogen of asparagine. An N-linked glycan of the invention preferably has the following structure:

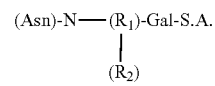

wherein (Asn) is one or more naturally or non-naturally occurring asparagine residues which has been modified by the addition of said N-linked glycan;

wherein S.A. is a sialic acid;

wherein, $R_1$ is H, or $(GlcNAc)_n$, where n=1, 2, 3, 4, 5, 6, 7, 8, 9, or 10;

and wherein when $R_1$ is (GlcNAc), $R_2$ is H, or S.A.

In a preferred embodiment, an N-linked glycan can also be a branched glycan having the following basic structure:

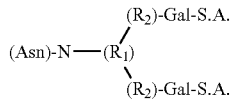

wherein (Asn) is one or more non-naturally occurring asparagine residues which has been modified by the addition of said N-linked glycan;

wherein S.A. is a sialic acid;

wherein $R_1$ is H, $(GlcNAc)_n$, or $(GlcNAc)_n$ linked to mannose, wherein n=1, 2, 3, 4, 5, 6, 7, 8, 9, or 10;

wherein $R_2$ is H, mannose, $(GlcNAc)_n$, or mannose linked to $(GlcNAc)_n$, wherein n=1, 2, 3, 4, 5, 6, 7, 8, 9, or 10.

In a preferred embodiment the branched N-linked glycan has the following structure:

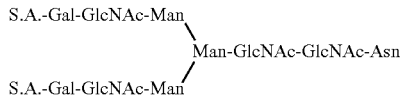

In addition to the branched N-linked glycan structures shown above, the invention also contemplates that an N-linked glycan useful in the invention may be a branched glycan with more than the two branches shown above, but which has three, four and up to five or more branches. For example, the base chain (Asn)-N—($R_1$) may be linked to three, four, and up to five or more ($R_2$)-Gal-S.A. branches, wherein the $R_1$ and $R_2$ moieties are defined as described above.

N-linked glycans useful in the invention are known in the art (see, e.g., Mattu et al., 1998, The Journal of Biological Chemistry, Vol. 273, No. 4, 2260-2272). Similar to O-linked glycans, N-linked glycans coupled to IgA1 binding proteins may be produced using methods known in the art, or may be obtained from commercial sources.

Regardless of whether the IgA1 binding protein is coupled to an O- or N-linked glycan, an important feature of the glycan is that the terminal residue on the glycan chain should be S.A. and the second to last residue on the chain should be galactose. Otherwise, the remaining structure is not specifically restricted, and may be chosen by one of skill in the art based on considerations of binding sites, size, occlusion of the IgA1 binding site, and tertiary interactions with either IgA1 or the IgA1 binding protein.

IgA1 Binding

According to the present invention, IgA1 binding proteins are generated which are linked to either or both of O- or N-linked glycans and which can specifically bind to IgA1 or a portion thereof. Specifically binds, as used herein refers to the interaction of two molecules, e.g., IgA1 and an IgA1 binding protein, wherein the interaction is dependent upon the presence of particular structures on the respective molecules. For example, when the two molecules are protein molecules, a structure on the first molecule (i.e., IgA1 binding protein) recognizes and binds to a structure on the second molecule (i.e., IgA1), rather than to proteins in general. Specific binding means that a molecule binds its specific binding partner with at least 2-fold greater affinity, and preferably at least 10-fold, 20-fold, 50-fold, 100-fold or higher affinity than it binds a non-specific molecule. Alternatively, specifically binds as used herein refers to the binding of two protein molecules to each other with a dissociation constant ($K_d$) of 1 µM or lower. For example, the affinity or $K_d$ for a specific binding interaction can be about 1 µM, or lower, about 500 nM or lower, and about 300 nM or lower. Preferably the $K_d$ for a specific binding interaction is about 300 nM or lower. Specific binding between two molecules (e.g., protein molecules) can be measured using methods known in the art. For example, specific binding may be determined as measured by surface plasmon resonance analysis using, for example, a BIAcore™ surface plasmon resonance system and BIAcore™ kinetic evaluation software (e.g., version 2.1).

More specifically, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of IgA1 polypeptide from the aqueous phase to a IgA1 binding protein immobilized in a membrane on the sensor. This change in mass is measured as resonance units versus time after injection or removal of the IgA1 binding protein and is measured using a Biacore Biosensor (Biacore AB). IgA1 or a binding protein thereof can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for IgA1 binding to an IgA1 binding protein in an SPR assay can be fine-tuned by one of skill in the art using the conditions reported by Sarrio et al. as a starting point.

SPR can assay for modulators of binding in at least two ways. First, IgA1 polypeptide can be pre-bound to immobilized IgA1 binding protein, followed by injection of candidate modulator (i.e., a competitor such as a second IgA1 binding protein) at approximately 10 µl/min flow rate and a concentration ranging from 1 nM to 100 µM, preferably about 1 µM. Displacement of the bound IgA1 can be quantitated, permitting detection of modulator binding. A decrease of 10% or more in the amount of a IgA1 polypeptide bound is in the presence of candidate modulator, relative to the amount of IgA1 bound in the absence of candidate modulator indicates that the candidate modulator inhibits the interaction of IgA1 to the first IgA1 binding proteins and identifies the candidate modulator as a second IgA1 binding protein.

Another method of measuring of binding of IgA1 to an IgA1 binding protein uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g., IgA1 polypeptide and an IgA1 binding polypeptide, are labeled with a complementary pair of donor and acceptor fluorophores. While bound closely together by the IgA1/IgA1 binding protein interaction, the fluorescence emitted upon excitation of the donor fluorophore will have a different wavelength than that emitted in response to that excitation wavelength when the polypeptides are not bound, providing for quantitation of bound versus unbound polypeptides by measurement of emission intensity at each wavelength; that is, the excitation of the donor fluorophore results in an emission wavelength which is similar to that of the excitation wavelength of the acceptor fluorophore. Thus excitation of the donor causes emission from the acceptor. This energy transfer will only occur, and is thus only detectable when the IgA1 and IgA1 binding protein are bound together. Donor:Acceptor pairs of fluorophores with which to label the polypeptides are well known in the art. Of particular interest are variants of the *A. Victoria* GFP known as Cyan FP (CFP, Donor(D)) and Yellow FP (YFP, Acceptor(A)). The GFP variants can be made as fusion proteins with the respective members of the binding pair to serve as D-A pairs in a FRET scheme to measure protein-protein interaction. Vectors for the expression of GFP variants as fusions are known in the art.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore: quencher pair; that is, quenching of the fluorescent emission is indicative of the binding of one peptide to the other peptide.

Another alternative for monitoring IgA1 and IgA1 binding protein interactions uses a biosensor assay. ICS biosensors have been described by AMBRI (Australian Membrane Biotechnology Research Institute). In this technology, the association of macromolecules (e.g., IgA1 and a binding protein) is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries, but may be adapted by one of skill in the art to measure binding of IgA1 and an IgA1 binding protein.

Any of the binding assays described herein, may be used to identify additional IgA1 binding proteins in addition to those specifically disclosed herein. For example, a candidate IgA1 binding protein may be placed in contact with IgA1 in the context of one or more of the above binding assays, and the amount of binding detected. If the level of binding of the candidate IgA1 binding protein is not more than 10% less than that of a known IgA1 binding protein (e.g., Sir22), then the candidate is identified as an IgA1 binding protein.

Other assays to measure whether a particular protein or polypeptide is an IgA1 binding protein include in vivo assays in which a candidate binding protein is administered to an individual, and after a period of time (described further below) a blood, plasma, or serum sample is obtained from the individual and assayed for the amount of circulating IgA1 (e.g., by using standard immunoassay or ELISA with an anti-IgA1 antibody, the methods for which are known in the art). A decrease in the amount of circulating IgA1 of at least 10% relative to the amount of IgA1 in an individual not administered the candidate binding protein indicates that the candidate is a protein which specifically binds IgA1.

Method for Decreasing IgA1/Treating IgA1 Deposition Disease

The present invention provides a method for decreasing the amount of IgA1 in an individual by administering to the individual an O- or N-linked glycan modified IgA1 binding protein as described herein. It is envisioned that administration of glycan-modified IgA1 binding proteins will result in binding to human IgA. Since the IgA1 binding protein contains O-linked glycans, the target IgA1 protein will acquire carbohydrate residues that will promote its removal by hepatic asialoglycoprotein receptors (ASGPR; see description of ASGPR above). It is thought that desialylation of the added oligosaccharide will occur as it does to normal IgA (a normal catabolic event for all circulating glycoproteins), and this will expose underlying Gal sugar moiety which is the recognition signal for ASGPR binding. The infused glycan-modified IgA1 binding protein, then, is intended to guide what would be an undergalactosylated IgA1 toward disposal, restoring its clearance rate toward normal, and preventing prolonged circulation that favors pathogenic tissue deposition. The compound may also result in elution of IgA already in the tissues. Thus, the present invention also encompasses a method for the treatment of a disease state characterized by IgA1 deposition in tissues. Administration of the glycan-modified IgA1 binding proteins of the invention may be used to remove accumulated IgA1 from tissues or remove circulating IgA1, thus decreasing the amount of IgA1 available for deposition, thereby decreasing IgA1 deposition and treating IgA1 deposition disease.

IgA1 Deposition Diseases

Herein, IgA1 binding proteins are used as therapeutic agents to treat IgA1 deposition diseases. The abnormal deposition of IgA1 molecules is known to cause renal failure, skin blistering, rash, arthritis, gastrointestinal bleeding and abdominal pain.

IgA Nephropathy

In one embodiment, the invention provides a method for treating IgA nephropathy by administering to a patient in need of such treatment an IgA1 binding protein comprising O- or N-linked glycan. IgA nephropathy is a disease of the kidney. The disease is considered to be an immune-complex-mediated glomerulonephritis, which is characterized by granular deposition of IgA1 in the glomerular mesangial areas. Nephropathy results and is defined by proliferative changes in the glomerular mesangial cells.

IgA nephropathy is one of the most common types of chronic glomerulonephritis and a frequent cause of end-stage renal disease. In addition, mesangial proliferation and extracellular matrix expansion are a common pathologic feature, and both correlate with the extent of renal injury. These changes are stimulated by the pro-inflammatory cytokine IL-6, and fibrosis by TGF-beta and other cytokines. As discussed above, the interaction of deposited IgA1 with FcαR may trigger release of cytokines, and other immunoglobulins such as IgG and IgM and complement components in the renal deposits may be important in causing injury. But dominance of IgA1 defines the disease.

Dermatitis Herpetiformis

The invention further provides a method for treating dermatitis herpetiformis (DH) by administering to a patient in need of such treatment a glycan-modified IgA1 binding protein. Dermatitis herpetiformis is a chronic blistering skin disease associated with deposits of IgA1 at the dermal-epidermal junction (Hall, R P & T. J. Lawley, J. Immunol. (1985) 135 (3): 1760-5). DH patients have granular IgA1 deposits and have an associated gluten-sensitive enteropathy (GSE).

Henoch-Schoenlein Purpura

In another embodiment, the invention provides a method for treating Henoch-Schoenlein purpura (HS) by administering to a patient in need of such treatment a glycan-modified IgA1 binding protein. Henoch-Schoenlein purpura is a skin and kidney disease. HSP is characterized by deposition of IgA1-containing immune complexes in tissue. The disease is diagnosed by observing evidence of IgA1 deposition in the blood vessel walls or kidney mesangium via immunofluorescence microscopy. The clinical manifestations typically include rash; arthralgias; abdominal pain; and renal disease.

Animal Models

The therapeutic effect of glycan-linked IgA binding proteins of the present invention can be tested in any suitable animal model known to those skilled in the art. Some exemplary animal models are described below.

1. IgA Nephropathy

A number of rat and mice animal models of IgA nephropathy are available and are useful in the present invention. According to the invention, however, such animal models are particularly useful where the model animal comprises abnormally glycosylated IgA1. Abnormal glycosylation of IgA1 can be achieved enzymatically as described below. These models are described in Emancipator, S. N. et al., (1987) Animal models of IgA nephropathy In IgA nephropathy. A. R. Clarkson, editor. Martinus Nijhoff publishing, Boston. 188-203, herein incorporated by reference in its entirety. An exemplary model is described in Gesualdo L. et al, (1990) J. Clin. Invest. 86: 715-722, also herein incorporated in its entirety. Briefly, an IgA antibody/dextran sulfate complex is injected into mice. The immuno-complex lodges in the kidney and the mice present with glomerulonephritis that resembles typical cases of human IgA nephropathy. It is preferred that in the above models, human IgA1 is introduced and expressed in the model as described further in the Examples. How the model is made and used for testing therapeutic agents is described in more detail below.

Soluble immune complexes of dextran sulfate (500 kD, Sigma Chemical Co., St. Louis, Mo.) and monoclonal IgA anti-β1-6 glycoside (J558: Litton Bionetics, Kensington, Md.) are prepared at threefold excess (26.5 μg dextran/mg J558 (Nephropathy model); 22.0 μg dextran/mg MOPC 104 E (normal control)). Complexes containing 3 mg antibody are injected into Swiss-Webster mice via tail vein injection. After 1 hour, the point of maximal deposition of IgA complexes in the kidney, mice are injected intraperitoneally with multiple doses of either saline or therapeutic agent at given intervals, such as 10 minute intervals. The mice are killed 1 hour after the last injection.

Kidneys are then isolated from each mouse to look at IgA1 deposition and morphology by light, immunofluoresence, and electron microscopy.

Briefly, to monitor IgA1 deposition, snap-frozen samples of renal cortex, cryostat sectioned at 4 um, are stained with fluoresceinated IgG fractions of goat antisera specific for mouse IgA (US Biochemical Corp) by direct immunofluoresence to semiquantitatively score for IgA1 deposits (Nakazawa, M. et al., (1986) Lab. Invest. 55:551-556, and Nakazawa, M. et al., (1986) J. Exp. Med. 164:1973-1987). A therapeutic agent (e.g., a glycan-linked IgA1 binding protein) is regarded as an effective agent when the number of IgA1 deposits scored is reduced towards the number of IgA1 deposits observed in a normal kidney.

Morphological changes, such as expansion of mesangial matrix and mesangial hypercellularity, is scored by staining sections of renal cortex with PAS reagent (Gesualdo, L. et al, (1990) J. Clin. Invest. 86: 715-722). Briefly, renal cortex is fixed in 10% formalin, embedded in paraffin and stained. Expansion of mesangial matrix and mesangial hypercellularity is scored semiquantitatively according to the methods described in Nakazawa, M. et al. (1986) Lab. Invest. 55:551-556, and Nakazawa, M. et al. (1986) J. Exp. Med. 164:1973-1987, herein incorporated by reference in their entirety.

Normal mesangial matrix is scored as 0. Expansion of mesangial matrix is scored as +1 when widened mesangial stalks are observed, +2 when matrix encroachment on capillary lumens is observed, and +3 when conspicuous widening of mesingial stalk is observed along with a decrease in capillary lumen. A therapeutic agent (e.g., glycan-linked IgA1 binding protein) is regarded as effective agent when the expansion of mesangial matrix is reduced towards the morphology of the matrix observed in a normal kidney, for example to a score of +2, or +1, or 0.

Normal mesangial cellularity is scored as 0 and is defined as 3 or fewer cell nuclei per mesangial area. Hypercellularity is scored as +1 when 4 to 6 cell nuclei per mesangial area are observed, as +2 when 4 to 6 cell nuclei per mesangial area are observed in most areas but some areas have 7 or more nuclei, and as +3 when 7 or more cell nuclei per mesangial area are observed in most areas. A therapeutic agent (e.g, glycan-linked IgA1 binding protein) is regarded as effective agent when the mesangial hypercellularity is reduced towards that observed in a normal kidney, for example to a score of +2, or +1, or 0.

Total glomerular area, matrix area, and glomerular cellularity are also quantified in randomly selected glomeruli from each mouse by computer morphometry (Cue image analysis system, Olympus Corp., Columbia, Md.) (Gesualdo L. et al, (1990) J. Clin. Invest. 86: 715-722). Briefly, cubes of cortex are fixed in 2.5% gluteraldehyde in 0.1 M sodium cacodylate, post fixed in 1% $OsO_4$, and embedded in Spurr's epoxy (Polysciences, Inc. Warrington, Pa.). 50-70 nm sections are stained with uranyl acetate and lead hydroxide. Coded grids are examined in a JEOL JEM 100 EX microscope and matrix, cellularity, and immune deposits are semiquantified as described in Nakazawa, M. et al., (1986) J. Exp. Med. 164: 1973-1987, herein incorporated by reference in its entirety.

Hematuria (the presence of red blood cells in urine) and proteinura (the presence of protein in urine) are also a suitable measure of IgA nephropathy. Briefly, mice are placed in metabolic cages and urine is collected for 24 hours. The urine is then centrifuged and assayed for protein by turbidimetry in 3% sulfalicylic acid and hematuria by microscopy, as described in Nakazawa, M. et al., (1986) J. Exp. Med. 164: 1973-1987, herein incorporated by reference in its entirety. Typically, a normal mouse without IgA nephropathy will have less then three red blood cells per high power field (40×), while mice with IgA nephropathy will have greater than 10 red blood cells per high power field. A reduction in the number of red blood cells per high power field is indicative that the therapeutic agent is effective for IgA nephropathy. Mice are tested for hematuria and proteinura before treatment to determine the reference value indicative of disease. A reduction in the reference value, as compared to the value for hematuria and proteinura obtained before treatment, of 5%, 10%, 30%, 40% preferably 50%, and more preferably greater than 50% after treatment with the glycan-linked IgA1 binding protein is indicative that the agent is effective for treatment of IgA1 Nephropathy.

In a preferred embodiment, animal testing may be performed according to the following general protocol, and using the following animal model to measure whether the O-glycan or N-glycan modified IgA1 binding polypeptides will improve underglycosylated IgA1 clearance. Polyclonal human dimeric IgA1 (dIgA1) is purified from outdated, pooled blood bank sera that is rendered 50% saturated by adding solid $(NH_4)_2SO_4$. The washed precipitate is dissolved and dialyzed against PBS, pH 7.2, and then passed through a Sephacryl 300 column. Fractions containing dIgA are pooled. To separate IgA1 from IgA2, pooled dIgA is applied to a column of immobilized jacalin (an IgA1-binding lectin that detects de-sialyated O-glycans at hinge region) in PBS. dIgA1 is eluted with 0.25M D-galactose and dialyzed against PBS, concentrated, and stored at 4° C. The human dIgA1 is then digested by neuraminidase from *Vibrio cholerae* (or other sources, e.g., *Clostridia* species) to remove NeuNAc, and further digested with β-galactosidase from bovine testis to remove Gal residues. The Gal-depleted dIgA molecules are then radiolabeled with $^{125}$I or with other tracking methods, and then preincubated with and without one of O- or N-glycan modified IgA1 binding polypeptides described herein. After injection into mice via tail vein, the clearance rate in the form of decreasing of radioactivity will be measured by taking blood samples at different time-intervals. These measurements will reflect how fast these radiolabeled and deglycosylated human dIgA1 that complexed with or without O- or N-glycan modified IgA1 binding polypeptides will be cleared away from blood stream by animals' ASGP receptors.

Dosage and Administration

Accordingly, one or more IgA1 binding proteins as described herein are modified by the methods known in the art and described above to include, linked to either Ser/Thr or Asn residues present therein, O- or N-linked glycan molecules, respectively. In one embodiment, where the IgA1 binding protein is CD89 in a soluble form, no additional glycan molecules are attached. It is known in the art that CD89 is already glycosylated, and thus one of skill in the art practicing the claimed invention would not have to add additional glycan moieties to CD89.

The glycosylated IgA1 binding protein may be administered to an individual by any method known in the art. The glycan-linked IgA1 binding protein of the present invention can be used in a composition that is combined with a pharmaceutically acceptable carrier. Such a composition may also contain diluents, fillers, salts, buffers, stabilizers, solubilizers, and other materials well known in the art.

In an alternate embodiment, the pharmaceutical formulation may include two or more different glycan-linked IgA1 binding protein, administered together or sequentially, providing a synergistic effect. For example, an anti-IgA1 Fab linked to one or more glycan moieties may be combined with a Sir22 which is also linked to one or more glycan moieties. Such combined or sequential administration of different proteases may be useful because the binding proteins may interact with (e.g., bind to) the IgA1 substrate in different ways, thus providing an advantage over single IgA1 binding protein administration.

The term "pharmaceutically acceptable" means a non-toxic material that does not interfere with the effectiveness of the biological activity of the active ingredient(s). The characteristics of the carrier will depend on the route of administration. Such carriers include, but are not limited to, saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, tablets may be coated with a material such as glyceryl monostearate or glyceryl distearate, to delay absorption in the gastrointestinal tract.

Pharmaceutically acceptable salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The composition may also contain other agents, which either enhance the activity of the composition, or compliment its activity or use in treatment, or maintain the activity of the therapeutic agent in storage. Such additional factors and/or agents may be included in the composition to produce a synergistic effect or to minimize side effects. Additionally, administration of the composition of the present invention may be administered concurrently with other therapies.

Administration of the therapeutic agent of the present invention can be carried out in a variety of conventional ways, such as oral ingestion, inhalation, topical application or cutaneous, subcutaneous, intraperitoneal, parenteral or intravenous injection.

The compositions containing the therapeutic agent (e.g., a glycan-linked IgA1 binding protein) of the present invention can be administered intravenously, as by injection of a unit dose, for example. The term "unit dose" when used in reference to a glycan-linked IgA1 binding protein or therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

Modes of administration of the glycan-linked IgA1 binding proteins of the present invention include intravenous, intramuscular, intraperitoneal, intrasternal, subcutaneous and intra-arterial injection and infusion; preferably intravenous injection. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents, and/or compounds to shield the immunogenic determinant of the therapeutic agent. Prevention of the action of microorganisms may be improved by the inclusion of various antibacterial and antifungal agents such as paraben, chlorobutanol, phenol sorbic acid and the like. It may also be desirable to include isotonic agents such as sugars, sodium chloride and the like. Prolonged absorption of an injectable pharmaceutical form may be brought about by the inclusion of agents, such as aluminum monostearate and gelatin, which delay absorption. Injectable depot forms are made by forming microencapsule matrices of the therapeutic agent in biodegradable polymers such as polylactide-polyglycolide, poly(orthoesters) and poly(anhydrides). Depending upon the ratio of therapeutic agent to polymer and the nature of the particular polymer employed, the rate of therapeutic agent release can be controlled. Injectable formulations are also prepared by entrapping the therapeutic agent in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers. Extemporaneous injection solutions and suspensions may be prepared from sterile powders, granules and tablets of the kind previously described.

As used herein, a "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. Generally, a composition will be administered in a single dose in the range of 100 µg-10 mg/kg body weight, preferably in the range of 1 µg-100 µg/kg body weight. This dosage may be repeated daily, weekly, monthly, yearly, or as considered appropriate by the treating physician.

When a therapeutically effective amount of a glycan-linked IgA1 binding protein of the present invention is administered orally, the composition of the present invention can be in the form of a liquid, the composition contains from about 0.5 to 90% by weight of protein of the present invention, and preferably from about 1 to 50% protein of the present invention.

When a therapeutically effective amount of a glycan-linked IgA1 binding protein of the present invention is administered by intravenous, cutaneous or subcutaneous injection, the protein will be in the form of a pyrogen-free, parenterally acceptable aqueous solution. The preparation of such parenterally acceptable protein solutions, having due regard to pH, isotonicity, stability, and the like, is within the skill in the art. A preferred composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art.

Topical administration, in which the composition is brought in contact with tissue(s), may be suitable for dermatitis herpetiformis. By "contacting" is meant not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The amount of a glycan-linked IgA1 binding protein of the present invention in the pharmaceutical composition of the present invention will depend upon the nature and severity of the condition being treated, and on the nature of prior treatments, which the patient has undergone. Ultimately, the attending physician will decide the amount of the therapeutic agent of the present invention with which to treat each individual patient. Initially, the attending physician will administer low doses of the therapeutic agent of the present invention and observe the patient's response. Larger doses of may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the therapeutic agent of the present invention will be in the range of 12 to 72 hours of continuous intravenous administration, at a rate of approximately 30 mg/hour. Ultimately the attending physician will decide on the appropriate duration of intravenous therapy using the pharmaceutical composition of the present invention.

Determining the Effectiveness of Administration

The glycan-linked IgA1 binding proteins of the invention may be administered to an individual to decrease or reduce the amount of IgA1 in the individual, preferably reducing the amount of circulating IgA1, still more preferably decreasing the amount of abnormally glycosylated in the individual, and/or may be administered to treat a disease characterized by IgA1 deposition.

Decreased or reduced IgA1 in an individual may be measured by any one of several methods known to those of skill in the art. IgA1 levels may be measured from biological samples from an individual. Such samples may comprise tissue samples, whole cells, cell lysates, or isolated nucleic acids, including, for example, needle biopsy cores, surgical resection samples, lymph node tissue, or serum. In one embodiment, the biological sample is a blood sample or serum sample. Methods for identifying the amounts of abnormally glycosylated IgA1 in an individual are known in the art and may be found, for example in U.S. Pat. No. 6,429,024 (the entirety of which is incorporated herein by reference). In particular, U.S. Pat. No. 6,429,024 provides antibody polypeptides which selectively bind to abnormally glycosylated IgA1 relative to normally glycosylated IgA1.

Antibody polypeptides which specifically recognize IgA1 (e.g., such as an anti-IgA1 Fab) may be used to detect the presence of IgA1 in a clinical sample by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells comprising IgA1 in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4 C, adding protein A and/or protein G sepharose beads to the cell lysate, incubating for about an hour or more at 4 C, washing the beads in lysis buffer and resuspending the beads in SDS/sample buffer. In the case of immunoprecipitation of a serum sample, however the above protocol is carried out absent the cell lysis step. The ability of the anti-IgA1 antibody polypeptide to immunoprecipitate IgA1 antigen can be assessed by, e.g., western blot analysis. The parameters that can be modified to increase the binding of the antibody to an antigen and decrease the background (e.g., preclearing the cell lysate with sepharose beads) are well known to those of skill in the art (Ausubel et al, supra).

IgA1 may be detected in a patient clinical sample using Western blot analysis. Briefly, Western blot analysis comprises preparing protein samples, electrophoresis of the protein samples in a polyacrylamide gel (e.g., 8%-20% SDS-PAGE), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an antihuman antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. Methods for the optimization of such an analysis are well known in the art (Ausubel, et al., supra).

Alternatively, the presence of IgA1 in a clinical sample may be detected by ELISA. ELISAs comprise preparing antigen, coating the well of a 96 well microtiter plate (or other suitable container) with the IgA1, adding an anti-IgA1 antibody polypeptide conjugated to a detectable compound such as an enzymatic substrate (e.g., horseradish peroxidase or alkaline phosphatase) to the well and incubating for a period of time, and detecting the presence of IgA1. In ELISAs the anti-IgA1 antibody polypeptide does not have to be conjugated to a detectable compound; instead, a second antibody (which recognizes the IgA1 antibody polypeptide) conjugated to a detectable compound may be added to the well. This method may be modified or optimized according techniques which are known to those of skill in the art.

Immunoassays, useful in the present invention include those described above, and can also include both homogeneous and heterogeneous procedures such as fluorescence polarization immunoassay (FPIA), fluorescence immunoassay (FIA), enzyme immunoassay (EIA), and nephelometric inhibition immunoassay (NIA).

In one embodiment, tissue samples may be used to measure the amount of IgA1 by immunohistochemical staining which may be used to determine the amount of IgA1, for example in kidney mesangial tissue. For such staining, a multiblock of tissue is taken from the biopsy or other tissue sample and subjected to proteolytic hydrolysis, employing such agents as protease K or pepsin.

The tissue samples are fixed by treatment with a reagent such as formalin, glutaraldehyde, methanol, or the like. The samples are then incubated with an antibody, preferably a monoclonal antibody, with binding specificity for IgA1. This antibody may be conjugated to a label for subsequent detection of binding. Samples are incubated for a time sufficient for formation of the immunocomplexes. Binding of the antibody is then detected by virtue of a label conjugated to this antibody. Where the antibody is unlabeled, a second labeled antibody may be employed, e.g., which is specific for the isotype of the anti-IgA1 polypeptide antibody. Examples of labels which may be employed include radionuclides, fluorescers, chemiluniinescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Other assays, known to those of skill in the art for determining the presence and/or quantity of a polypeptide in a sample (either serum or tissue) are also encompassed by the present invention.

In one embodiment, the invention relates to a method for treating a disease associated with IgA1 deposition disease. In addition to evaluating IgA1 deposition disease state using the methods above for detecting IgA1 (either in circulation or in tissue samples), the efficacy of a treatment of IgA1 deposition disease by glycan-linked IgA1 binding proteins may be evaluated by monitoring grossly observable aspects of the disease state itself. That is, any of the clinical manifestations of IgA1 deposition disease described above may be used as a marker for either treatment of IgA1 deposition disease and/or a reduction in IgA1 levels. A reduction in an individual having received one or more glycan-linked IgA1 binding proteins of the invention, in any one or more of the clinical manifestations of IgA1 deposition disease of at least 10% relative to the clinical symptom in that individual prior to receipt of glycan-linked IgA binding protein is indicative of treatment of the disease and/or a decrease in IgA1 levels. Preferably the observed clinical symptom is reduced by more than 10% in an individual which has received a glycan-linked IgA1 binding protein of the invention, preferably reduced by at least 20%, 30%, 40%, 50%, 60% or more, and up to 100% or more. The clinical scoring of the disease symptoms described above may be performed by a physician, nurse, or other person of ordinary skill in the art of diagnosing and scoring such symptoms.

As set out above, one aspect of the present invention relates to methods for decreasing the amount of IgA1 in an individual. As assessed by the assays set out above (or other comparable assays known to those of skill in the art), IgA1 is decreased (or reduced) in an individual if the amount of IgA1 measured in the individual following receipt of a glycan-linked IgA1 binding protein of the invention is at least 10% less than the amount of IgA1 measured in the same individual prior to the administration of the glycan-linked IgA1 binding protein. Preferably IgA1 is reduced by more than 10% in an individual which has received a glycan-linked IgA1 binding protein of the invention, preferably reduced by at least 20%, 30%, 40%, 50%, 60% or more, and up to 100% or more.

EXAMPLES

Example 1

In one embodiment, the present invention provides a method to develop a human antibody polypeptide (equivalent to Fab fragment) modified with O-glycans that specifically binds to human IgA1 hinge region sequence: TPPTPSPST-PPTPSPS (SEQ ID NO: 12).

Step 1: Antigen preparation. Chemical synthesis of a 16-mer peptide chain containing the sequence: Ac-Thr-Pro-Pro-Thr-Pro-Ser-Pro-Ser-Thr-Pro-Pro-Thr-Pro-Ser-Pro-Ser-OH (SEQ ID NO: 12). Purify the peptide by HPLC.

Step 2: Isolation of antibodies from a phage antibody library that have specificity for the peptide. The phage antibody library and related techniques were developed by Cambridge Antibody Technology (Granta Park, Cambridge, UK) and are known in the art. Briefly, a library contains many millions of phages that are engineered to display different antigen-specific antibody proteins on their surface. These antibodies are all encoded with genes of human origin. Therefore a specific antibody isolated from the library is viewed as of human origin. To find these antibodies in the library it will be probed with our synthesized peptide as a target antigen. A few phage antibodies that tightly bind to the peptide antigen will be isolated.

Step 3: Gene modification of isolated phage antibodies. After isolation of phage antibodies, the genes of the antibodies will be modified by site-directed mutagenesis technology known in the art. This includes, but is not limited to, two mutations desired to modify genes that encode H chains. a) We will introduce stop codon(s) at the end of the CH1 domain such that isolated phages will express truncated H chains which will assemble with L chains to form Fab fragments of these antibodies. b) At the end of CH1 region but before the stop codon we will introduce codons that encode amino acid sequences such as TPSPS in which Thr and Ser residues will provide sites that are suitable for addition of O-linked glycans. Methods for modification of antibody polypeptides, such as by site directed mutagenesis are known in the art, and may be found, for example, in Current Protocols in Molecular Biology.

Step 4: Production and purification of phage-derived Fab fragments. Purification of phage-derived Fab fragments may require up to three purification steps. a) sizing chromatography (gel filtration) to obtain fractions that consist only of dimerized polypeptide. (Note: it may happen that L-L or H—H dimers could be formed other than the desired H-L). Monomers or polymers other than a dimer would also need to be excluded. b) Affinity chromatography using anti-L chain antibody (kappa or lambda specificity needs to be determined). c) Affinity chromatography using immobilized anti-H chain.

Step 5: Conjugation of O-linked glycans onto Fab fragments can be done by chemical solid phase methods, enzymatic methods, or chemoenzymatic methods known in the art. For example, to conjugate O-linked glycans having the structure Thr/Ser-O-GalNAc-β1,3-Gal-α2,3-Sialic acid) onto Ser and/or Thr residues at the end of the CH1 domains, a two-step method could be used. Step 1 uses chemical synthesis to introduce T antigen (Thr/She-O-GalNAc-β1,3-Gal) onto the polypeptide, and after deprotection, sialic acids are added enzymatically. (See, e.g., Blixt et al., J Am Chem. Soc. 2002 May 22; 124 (20):5739-46.) The T antigen may be chemically synthesized using methods known in the art (see, for example, Hojo and Nakahara, Curr Protein Pept Sci. 2000 July; 1 (1):23-48; Danishefsky and Allen, Angew Chem Int Ed Engl. 2000 March; 39 (5):836-863). The enzymatic method to add the sialic acids onto T-antigen can be achieved with the use of recombinant sialytransferase ST3Gal I. The use of this enzyme for this purpose is described in Blixt et al., supra)

Step 6: Purification of Fab fragments now modified by O-linked glycans. This can be done by a two-step procedure involving jaclin affinity chromatography followed by ion exchange chromatography. Jacalin is a lectin (freely available commercially) that recognizes Gal residues on the glycans added to Fab. After this lectin chromatography step, the material will be further purified by ion-exchange chromatography, made efficient by the presence of sialic acid residues that lower the pI of the modified Fab.

Step 7: Test O-glycosylated Fab fragments in an animal model to evaluate its ability to clear partially deglycosylated human dIgA1.

Polyclonal human dimeric IgA1 (dIgA1) is purified from outdated, pooled blood bank sera that is rendered 50% saturated by adding solid $(NH_4)_2SO_4$. The washed precipitate is dissolved and dialyzed against PBS, pH 7.2, and then passed through a Sephacryl 300 column. Fractions containing dIgA are pooled. To separate IgA1 from IgA2, pooled dIgA is applied to a column of immobilized jacalin (an IgA1-binding lectin that detects de-sialyated O-glycans at hinge region.) in PBS. dIgA1 is eluted with 0.25M D-galactose and dialyzed against PBS, concentrated, and stored at 4° C. The human dIgA1 is then digested by neuraminidase from *Vibrio cholerae* (or other sources, e.g., *Clostridia* species) to remove NeuNAc, and further digested with β-galactosidase from bovine testis to remove Gal residues. The Gal-depleted dIgA molecules are then radiolabeled with $^{125}$I or with other tracking methods, and then preincubated with and without the O-linked anti-IgA1 Fab described above. After injection into mice via tail vein, the clearance rate in the form of decreasing of radioactivity will be measured by taking blood samples at different time-intervals. These measurements will reflect how fast these radiolabeled and deglycosylated human dIgA1 that complexed with or without O- or N-glycan modified IgA1 binding polypeptides will be cleared away from blood stream by animals' ASGP receptors.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed herein.

SEQUENCE LISTING

<160> NUMBER OF SEQ ID NOS: 13

<210> SEQ ID NO 1
<211> LENGTH: 349
<212> TYPE: PRT
<213> ORGANISM: Streptococcus pyogenes

<400> SEQUENCE: 1

```
Met Ala Arg Lys Asp Thr Asn Lys Gln Tyr Ser Leu Arg Lys Leu Lys
  1               5                  10                  15

Thr Gly Thr Ala Ser Val Ala Val Ala Val Ala Val Leu Gly Ala Gly
             20                  25                  30

Phe Ala Asn Gln Thr Thr Val Lys Ala Glu Ser Ser Asn Asn Ala Glu
         35                  40                  45

Ser Ser Asn Ile Ser Gln Glu Ser Lys Leu Ile Asn Thr Leu Thr Asp
     50                  55                  60

Glu Asn Glu Lys Leu Arg Glu Glu Leu Gln Gln Tyr Tyr Ala Leu Ser
 65                  70                  75                  80

Asp Ala Lys Glu Glu Glu Pro Arg Tyr Lys Ala Leu Arg Gly Glu Asn
                 85                  90                  95

Gln Asp Leu Arg Glu Lys Glu Arg Lys Tyr Gln Asp Lys Ile Lys Lys
            100                 105                 110

Leu Glu Glu Lys Glu Lys Asn Leu Glu Lys Lys Ser Glu Asp Val Glu
        115                 120                 125

Arg His Tyr Leu Lys Lys Leu Asp Gln Glu His Lys Glu Gln Gln Glu
    130                 135                 140

Arg Gln Lys Asn Leu Glu Glu Leu Glu Arg Gln Ser Gln Arg Glu Ile
145                 150                 155                 160

Glu Lys Gln Ile Ser Glu Ala Ser Arg Lys Ser Leu Ser Arg Asp Leu
                165                 170                 175

Glu Ala Ser Arg Ala Ala Lys Lys Lys Val Glu Ala Asp Leu Ala Ala
            180                 185                 190

Leu Asn Ala Glu His Gln Lys Leu Lys Glu Glu Lys Gln Ile Ser Asp
        195                 200                 205

Ala Ser Arg Gln Gly Leu Ser Arg Asp Leu Glu Ala Ser Arg Glu Ala
    210                 215                 220

Lys Lys Lys Val Glu Ala Asp Leu Ala Glu Ala Asn Ser Lys Leu Gln
225                 230                 235                 240

Ala Leu Glu Lys Leu Asn Lys Glu Leu Glu Glu Gly Lys Lys Leu Ser
                245                 250                 255

Glu Lys Glu Lys Ala Glu Leu Gln Ala Arg Leu Glu Ala Glu Ala Lys
            260                 265                 270
```

```
Ala Leu Lys Glu Gln Leu Ala Lys Gln Ala Glu Glu Leu Ala Lys Leu
        275                 280                 285

Lys Gly Asn Gln Thr Pro Asn Ala Lys Val Ala Pro Gln Ala Asn Arg
    290                 295                 300

Ser Arg Ser Ala Met Thr Gln Gln Lys Arg Thr Leu Pro Ser Thr Gly
305                 310                 315                 320

Glu Ala Ala Asn Pro Phe Phe Thr Ala Ala Ala Thr Val Met Val
                325                 330                 335

Ser Ala Gly Met Leu Ala Leu Lys Arg Lys Glu Asn
            340                 345

<210> SEQ ID NO 2
<211> LENGTH: 49
<212> TYPE: PRT
<213> ORGANISM: Streptococcus pyogenes

<400> SEQUENCE: 2

Tyr Tyr Ala Leu Ser Asp Ala Lys Glu Glu Pro Arg Tyr Lys Ala
1               5                   10                  15

Leu Arg Gly Glu Asn Gln Asp Leu Arg Glu Lys Glu Arg Lys Tyr Gln
            20                  25                  30

Asp Lys Ile Lys Lys Leu Glu Glu Lys Glu Lys Asn Leu Glu Lys Lys
        35                  40                  45

Ser

<210> SEQ ID NO 3
<211> LENGTH: 2200
<212> TYPE: DNA
<213> ORGANISM: Streptococcus pyogenes

<400> SEQUENCE: 3
aagcttcagg agctcaaaaa ccagatacta aacctggcaa taaagaggtt ccaacaagac      60
catcacaaac aagaacaaac actaataaag ctcctatggc gcaaacaaag agacaattac     120
cgtcaacagg cgaagaaaca accaacccat tcttcactgc agcagcattg acagtgatcg     180
catctgcagg cgtacttgcc ctaaaacgca agaagaaaa ctaagtccaa cccacactat     240
tttttctagc ccaagaaaaa acaaaaaaaa gaggaagccc cttcctcttt ttttgaacga     300
ttggaaagca aaaaggtcaa aaggtactaa agtcccaaaa acctggtctt taccttttg     360
ccgcttattc tttagaatag aattattaga gagaagtctt agaaaatga ggctaattcc     420
ctaaagatga aaaataagg agcaaataat ggctagaaaa gatacgaata acagtattc     480
gcttagaaaa ttaaaaacag gtacagcatc agtagcggtc gctgtggctg ttttaggagc     540
aggctttgca aaccaaacaa cagttaaggc ggagtcatca ataatgcgg agtcatcaaa     600
catttctcaa gaaagcaaac taataaatac attgactgat gaaaatgaga actcagaga     660
agagctccaa cagtattatg cattaagtga tgctaaagaa gagaacctag gtataaagc     720
attgagaggc gaaaatcaag atcttcggga aaagaaaga aataccagg ataaaataaa     780
aaaattagaa gaaaaagaga aaacctaga aaaaaaatca gaagatgtag aacgtcacta     840
tcttaaaaaa ctagatcaag aacataaaga acaacaagaa cgtcaaaaaa atctagagga     900
actcgaacgt caaagtcaac gagaaataga caagcgttat caagaacaac tccaaaaaca     960
acaacaatta gaaacagaaa agcaaatctc agaagctagt cgtaagagcc taagtcgtga    1020
ccttgaagcg tctcgtgcag ctaagaaaaa agtagaagca gacctagctg ctcttaatgc    1080
tgagcaccaa aaactcaaag aggaaaaaca aatctcagac gcaagccgtc aaggcctaag    1140
```

```
ccgtgacctt gaagcgtctc gcgaagctaa gaaaaaagta gaagcagact tagccgaagc    1200
aaatagcaaa cttcaagccc ttgaaaaact aaacaaagag cttgaagaag gtaagaaatt    1260
atcagaaaaa gaaaaagctg agttacaagc aagactagaa gctgaagcaa aagctcttaa    1320
agagcaattg gctaaacaag ctgaagaact tgcaaaacta aaaggcaacc aaacaccaaa    1380
cgctaaagta gccccacaag ctaaccgttc aagatcagca atgacgcaac aaaagagaac    1440
gttaccgtca caggcgaag cagctaaccc attctttaca gcagcagctg caacagtgat    1500
ggtatctgca ggtatgcttg ctctaaaacg caaagaagaa aactaagcta ttagactgat    1560
gctaaagcta agagagaatc aaatgattct ctcttttga gtggctaagt aactaacaat    1620
ctcagttaga ccaaaaaatg gaatggttc aaaaagctgg cctttactcc ttttgattaa    1680
ccatatataa caaaaacatt agggaaataa tagtaatatt aagtttgttt cctcaataaa    1740
atcaaggagt agataatggc tagacaacaa accaagaaaa attattcact acggaaacta    1800 aaaccggta cggcttcagt agccgttgct ttgaccgttt tgggcgcagg ttttgcaaac    1860
caaacggaag taagagctga tgaagcagtt tctggaaaag tggaagtaaa agaaagtgaa    1920
aaagagacta agtataagac gttggcctta agaggtgaaa atgctgacct agaaacgta    1980 aatgcaaaat atttagagaa aattaacgca gaagaagaaa aaaataaaaa attagaaaaa    2040
gaaaaacaag agttagaaaa ccaagcccctt aactttcaag atgtaattga aactcaggaa    2100
aaagaaaaag aagatctcaa aacaacttta gctaaggcta ctaaagaaaa cgagatctca    2160
gaagctagcc gtaaagggtt aagccgagac ttagaagctt                          2200
```

<210> SEQ ID NO 4
<211> LENGTH: 273
<212> TYPE: PRT
<213> ORGANISM: Staphylococcus aureus

<400> SEQUENCE: 4

Met Glu Gln Arg Ile Thr Leu Lys Glu Ala Trp Asp Gln Arg Asn Gly
 1               5                  10                  15

Phe Ile Gln Ser Leu Lys Asp Asp Pro Ser Gln Ser Ala Asn Val Leu
            20                  25                  30

Gly Glu Ala Gln Lys Leu Asn Asp Ser Gln Ala Pro Lys Ala Asp Ala
        35                  40                  45

Gln Gln Asn Asn Phe Asn Lys Asp Gln Gln Ser Ala Phe Tyr Glu Ile
    50                  55                  60

Leu Asn Met Pro Asn Leu Asn Glu Ala Gln Arg Asn Gly Phe Ile Gln
65                  70                  75                  80

Ser Leu Lys Asp Asp Pro Ser Gln Ser Thr Asn Val Leu Gly Glu Ala
                85                  90                  95

Lys Lys Leu Asn Glu Ser Gln Ala Pro Lys Ala Asp Asn Asn Phe Asn
            100                 105                 110

Lys Glu Gln Gln Asn Ala Phe Tyr Glu Ile Leu Asn Met Pro Asn Leu
        115                 120                 125

Asn Glu Glu Gln Arg Asn Gly Phe Ile Gln Ser Leu Lys Asp Asp Pro
    130                 135                 140

Ser Gln Ser Ala Asn Leu Leu Ser Glu Ala Lys Lys Leu Asn Glu Ser
145                 150                 155                 160

Gln Ala Pro Lys Ala Asp Asn Lys Phe Asn Lys Glu Gln Gln Asn Ala
                165                 170                 175

Phe Tyr Glu Ile Leu His Leu Pro Asn Leu Asn Glu Glu Gln Arg Asn
            180                 185                 190

```
Gly Phe Ile Gln Ser Leu Lys Asp Asp Pro Ser Gln Ser Ala Asn Leu
        195                 200                 205
Leu Ala Glu Ala Lys Lys Leu Asn Asp Ala Gln Ala Pro Lys Ala Asp
    210                 215                 220
Asn Lys Phe Asn Lys Glu Gln Gln Asn Ala Phe Tyr Glu Ile Leu His
225                 230                 235                 240
Leu Pro Asn Leu Thr Glu Glu Gln Arg Asn Gly Phe Ile Gln Ser Leu
                245                 250                 255
Lys Asp Asp Pro Gly Asn Ser Arg Gly Ser Val Asp Leu Gln Ile Thr
            260                 265                 270
Asn

<210> SEQ ID NO 5
<211> LENGTH: 58
<212> TYPE: PRT
<213> ORGANISM: Staphylococcus aureus

<400> SEQUENCE: 5

Val Asp Asn Lys Phe Asn Lys Glu Thr Ile Gln Ala Ser Gln Glu Ile
1               5                   10                  15
Arg Leu Leu Pro Asn Leu Asn Gly Arg Gln Lys Leu Ala Phe Ile His
                20                  25                  30
Ser Leu Leu Asp Asp Pro Ser Gln Ser Ala Asn Leu Leu Ala Glu Ala
            35                  40                  45
Lys Lys Leu Asn Asp Ala Gln Ala Pro Lys
        50                  55

<210> SEQ ID NO 6
<211> LENGTH: 126
<212> TYPE: PRT
<213> ORGANISM: Homo sapiens

<400> SEQUENCE: 6

Asp Ile Val Met Thr Gln Ser Pro Leu Ser Leu Ser Val Thr Pro Gly
1               5                   10                  15
Glu Pro Ala Ser Ile Ser Cys Arg Ser Ser Gln Ser Leu Leu Arg Arg
                20                  25                  30
Asp Gly His Asn Asp Leu Glu Trp Tyr Leu Gln Lys Pro Gly Gln Ser
            35                  40                  45
Pro Gln Pro Leu Ile Tyr Leu Gly Ser Thr Arg Ala Ser Gly Val Pro
        50                  55                  60
Asp Arg Phe Ser Gly Ser Gly Ser Gly Thr Asp Phe Thr Leu Lys Ile
65                  70                  75                  80
Ile Arg Val Glu Ala Glu Asp Ala Gly Thr Tyr Tyr Cys Met Gln Asn
                85                  90                  95
Lys Gln Thr Pro Leu Thr Phe Gly Gln Gly Thr Arg Leu Glu Ile Lys
            100                 105                 110
Arg Thr Val Ala Ala Pro Ser Val Phe Ile Phe Pro Pro Ser
        115                 120                 125

<210> SEQ ID NO 7
<211> LENGTH: 109
<212> TYPE: PRT
<213> ORGANISM: Homo sapiens

<400> SEQUENCE: 7

Gln Ser Ala Leu Thr Gln Pro Arg Ser Val Ser Gly Ser Pro Gly His
1               5                   10                  15
```

```
Ser Val Thr Ile Ser Cys Ile Gly Thr Ser Ser Asn Val Gly Asp Tyr
            20                  25                  30

Lys Tyr Val Ser Trp Tyr Gln Gln His Pro Gly Lys Ala Pro Lys Leu
        35                  40                  45

Ile Ile Tyr Glu Val Ser Ser Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ile Gly Ser
                85                  90                  95

Tyr Val Phe Gly Thr Gly Thr Lys Val Ile Val Leu Gly
            100                 105

<210> SEQ ID NO 8
<211> LENGTH: 119
<212> TYPE: PRT
<213> ORGANISM: Homo sapiens

<400> SEQUENCE: 8

Gln Val Gln Leu Val Glu Ser Gly Gly Gly Val Val Gln Ala Gly Thr
1               5                   10                  15

Ser Leu Arg Leu Ser Cys Thr Ala Ser Ala Phe Asn Leu Ser Asp Tyr
            20                  25                  30

Ala Met His Trp Val Arg Gln Ala Pro Gly Lys Gly Leu Glx Trp Val
        35                  40                  45

Ala Leu Ile Ser Tyr Gly Gly Ser Asx Thr Tyr Tyr Ala Asp Ser Val
50                  55                  60

Arg Gly Arg Phe Thr Ile Ser Arg Asx Ile Ser Lys Asx Thr Leu Tyr
65                  70                  75                  80

Leu Glx Met Lys Thr Leu Arg Thr Glu Asp Thr Ala Val Tyr Tyr Cys
                85                  90                  95

Ala Lys Leu Ile Ala Val Ala Gly Thr Arg Asx Phe Trp Gly Gln Gly
            100                 105                 110

Thr Leu Val Thr Val Ser Leu
        115

<210> SEQ ID NO 9
<211> LENGTH: 353
<212> TYPE: PRT
<213> ORGANISM: Homo sapiens

<400> SEQUENCE: 9

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110
```

```
Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
        130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
                180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
        260                 265                 270

Arg Glu Lys Tyr Leu Thr Trp Ala Ser Arg Gln Glu Pro Ser Gln Gly
    275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 10
<211> LENGTH: 25
<212> TYPE: PRT
<213> ORGANISM: Homo sapiens

<400> SEQUENCE: 10

Thr Val Pro Cys Pro Val Pro Ser Thr Pro Pro Thr Pro Ser Pro Ser
1               5                   10                  15

Thr Pro Pro Thr Pro Ser Pro Ser Cys
            20                  25

<210> SEQ ID NO 11
<211> LENGTH: 159
<212> TYPE: PRT
<213> ORGANISM: Homo sapiens

<400> SEQUENCE: 11

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60
```

```
Pro Leu Asn Asn Arg Glu Asn Ile Ser Asp Pro Thr Ser Pro Leu Arg
 65                  70                  75                  80

Thr Arg Phe Val Tyr His Leu Ser Asp Leu Cys Lys Lys Cys Asp Pro
                 85                  90                  95

Thr Glu Val Glu Leu Asp Asn Gln Ile Val Thr Ala Thr Gln Ser Asn
                100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
        130                 135                 140

Lys Met Val Glu Thr Ala Leu Thr Pro Asp Ala Cys Tyr Pro Asp
145                 150                 155

<210> SEQ ID NO 12
<211> LENGTH: 16
<212> TYPE: PRT
<213> ORGANISM: Homo sapiens

<400> SEQUENCE: 12

Thr Pro Pro Thr Pro Ser Pro Ser Thr Pro Pro Thr Pro Ser Pro Ser
1               5                   10                  15

<210> SEQ ID NO 13
<211> LENGTH: 6
<212> TYPE: PRT
<213> ORGANISM: Homo sapiens

<400> SEQUENCE: 13

Thr Pro Pro Thr Pro Ser
1               5
```

The invention claimed is:

1. An isolated antibody polypeptide which specifically binds IgA1, said polypeptide comprising one or both of (a) a naturally occurring or non-naturally occurring serine or threonine residue at the end of a CH1 domain, which serine or threonine residue has been artificially modified by addition of an O-linked glycan, and (b) a naturally occurring or non-naturally occurring asparagine residue at the end of a CH1 domain, which asparagine residue has been artificially modified by addition of an N-linked glycan;

(i) wherein the O-linked glycan has the following formula:

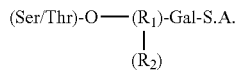

wherein, (Ser/Thr) is one of said one or more non-naturally occurring serine or threonine residues which has been modified by the addition of said O-linked glycan, wherein S.A. is a sialic acid, wherein, $R_1$ is H, $(GalNAc)_n$, where n =1, 2, 3, 4, 5, 6, 7, 8, 9, or 10, and wherein $R_2$ is H or S.A; and (ii) wherein the N-linked glycan has a formula selected from the group consisting:

(a)

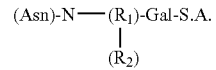

wherein (Asn) is one of said one or more non-naturally occurring asparagine residues which has been modified by the addition of said N-linked glycan, wherein S.A. is a sialic acid;

wherein, $R_1$ is H, $(GlcNAc)_n$, where n =1, 2, 3, 4, 5, 6, 7, 8, 9, or 10, and wherein $R_2$ is H or S.A; or (b) a biantennary structure having the formula:

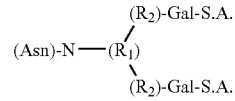

wherein (Asn) is one of said one or more non-naturally occurring asparagine residues which has been modified by the addition of said N-linked glycan, wherein S.A. is a sialic acid, wherein $R_1$ is H, $(GlcNAc)_n$, or $(GlcNAc)_n$ linked to mannose, wherein n =1, 2, 3, 4, 5, 6, 7, 8, 9, or 10, wherein $R_2$ is H, mannose, $(GlcNAc)_n$, or mannose linked to $(GlcNAc)_n$, wherein n=1, 2, 3, 4, 5, 6, 7, 8, 9, or 10.

2. The isolated antibody polypeptide of claim 1, wherein said antibody polypeptide is selected from the group consisting of a dAb, a Fab, an scFv, an Fv, or a disulfide-bonded Fv.

3. The isolated antibody polypeptide of claim 2, wherein said Fab is of human origin.

4. The isolated antibody polypeptide of claim 2, wherein said Fab is a fragment of a humanized chimeric monoclonal IgG.

5. The isolated antibody polypeptide of claim 1, wherein said antibody polypeptide binds to the hinge region of IgA1.

6. The isolated antibody polypeptide of claim 2, wherein said antibody polypeptide binds to the $CH_2$—$CH_3$ region interface of IgA1.

7. The isolated antibody polypeptide of claim 1, wherein said isolated antibody polypeptide specifically binds an IgA1 hinge region having the sequence TPPTPSPSTPPTPSPS (SEQ ID NO:12).

8. The isolated antibody polypeptide of claim 7, wherein said isolated antibody polypeptide specifically binds to GalNAc residues on said hinge region.

9. The isolated antibody polypeptide of claim 1, wherein said isolated antibody polypeptide binds to the J chain of a dimeric IgA.

10. The isolated antibody polypeptide of claim 1, wherein said isolated antibody polypeptide is artificially modified by chemical conjugation.

11. A method of reducing the amount of IgA1 in an individual, comprising administering to said individual an isolated antibody polypeptide of claim 1.

12. The method of claim 11, wherein said IgA1 is abnormally glycosylated.

13. The method of claim 11, wherein said antibody polypeptide is selected from the group consisting of a dAb, a Fab, an scFv, an Fv, or a disulfide-bonded Fv.

14. The method of claim 13, wherein said Fab is of human origin.

15. The method of claim 13, wherein said Fab is a fragment of a humanized chimeric monoclonal IgG.

16. The method of claim 13, wherein said antibody polypeptide binds to the hinge region of IgA1.

17. The method of claim 16, wherein said antibody polypeptide binds to the $CH_2$—$CH_3$ region interface of IgA1.

18. The method of claim 11, wherein said isolated antibody polypeptide specifically binds a IgA1 hinge region having the sequence TPPTPSPSTPPTPSPS (SEQ ID NO:12).

19. The method of claim 18, wherein said isolated antibody polypeptide specifically binds to GalNAc residues on said hinge region.

20. The method of claim 11, wherein said isolated antibody polypeptide binds to the J chain of a dimeric IgA.

21. The method of claim 11, wherein said N-linked glycan has the following formula:

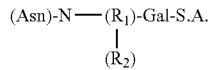

wherein (Asn) is one of said one or more non-naturally occurring asparagine residues which has been modified by the addition of said N-linked glycan;
wherein S.A. is a sialic acid;
wherein, $R_1$ is H, $(GlcNAc)_n$, where n =1, 2, 3, 4, 5, 6, 7, 8, 9, or 10;
and wherein $R_2$ is H or S.A.

22. The method of claim 11, wherein said N-linked glycan is a biantennary structure having the formula:

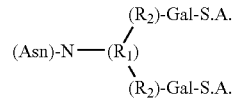

wherein (Asn) is one of said one or more non-naturally occurring asparagine residues which has been modified by the addition of said N-linked glycan;
wherein S.A. is a sialic acid;
wherein $R_1$ is H, $(GlcNAc)_n$, or $(GlcNAc)_n$ linked to mannose, wherein n =1, 2, 3, 4, 5, 6, 7, 8, 9, or 10;
and wherein $R_2$ is H, mannose, $(GlcNAc)_n$, or mannose linked to $(GlcNAc)_n$, wherein n =1, 2, 3, 4, 5, 6, 7, 8, 9, or 10.

23. A method for treatment of a disease characterized by IgA1 deposition, comprising administering to an individual in need thereof, an isolated antibody polypeptide of claim 1.

24. The method of claim 23, wherein said antibody polypeptide is selected from the group consisting of a dAb, a Fab, an scFv, an Fv, or a disulfide-bonded Fv.

25. The method of claim 23, wherein said Fab is of human origin.

26. The method of claim 23, wherein said Fab is a fragment of a humanized chimeric monoclonal IgG.

27. The method of claim 23, wherein said antibody polypeptide binds to the hinge region of IgA1.

28. The method of claim 23, wherein said antibody polypeptide binds to the $CH_2$—$CH_3$ region interface of IgA1.

29. The method of claim 23, wherein said isolated antibody polypeptide specifically binds a IgA1 hinge region having the sequence TPPTPSPSTPPTPSPS (SEQ ID NO:12).

30. The method of claim 29, wherein said isolated antibody polypeptide specifically binds to GalNAc residues on said hinge region.

31. The method of claim 23, wherein said isolated antibody polypeptide binds to the J chain of a dimeric IgA.

32. The method of claim 23, wherein said N-linked glycan has the following formula:

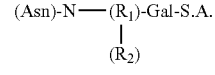

wherein (Asn) is one of said one or more non-naturally occurring asparagine residues which has been modified by the addition of said N-linked glycan;
wherein S.A. is a sialic acid;
wherein, $R_1$ is H, $(GlcNAc)_n$, where n =1, 2, 3, 4, 5, 6, 7, 8, 9, or 10;
and wherein $R_2$ is H or S.A.

33. The method of claim 23, wherein said N-linked glycan is a biantennary structure having the formula:

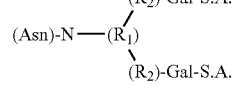

wherein (Asn) is one of said one or more non-naturally occurring asparagine residues which has been modified by the addition of said N-linked glycan;

wherein S.A. is a sialic acid;
wherein $R_1$ is H, (GlcNAc)., or (GlcNAc)$_n$, linked to mannose, wherein n =1, 2, 3, 4, 5, 6, 7, 8, 9, or 10;
and wherein $R_2$ is H, mannose, (GlcNAc)$_n$, or mannose linked to (GlcNAc)$_n$, wherein n =1, 2, 3, 4, 5, 6, 7, 8, 9, or 10.

* * * * *

UNITED STATES PATENT AND TRADEMARK OFFICE
CERTIFICATE OF CORRECTION

PATENT NO. : 8,440,191 B2
APPLICATION NO. : 12/094145
DATED : May 14, 2013
INVENTOR(S) : Plaut et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1320 days.

Signed and Sealed this
Eighth Day of September, 2015

Michelle K. Lee
*Director of the United States Patent and Trademark Office*